United States Patent [19]
Dobson, Jr.

[11] Patent Number: 5,629,298
[45] Date of Patent: May 13, 1997

[54] ADENOSINE AS A POSITIVE INOTROP IN THE COMPROMISED HEART

[75] Inventor: James G. Dobson, Jr., Shrewsbury, Mass.

[73] Assignee: University of Massachusetts Medical Center, Worcester, Mass.

[21] Appl. No.: 402,884

[22] Filed: Mar. 13, 1995

[51] Int. Cl.$^6$ .................. C07H 19/16; C07H 19/167
[52] U.S. Cl. ..................... 514/45; 514/46; 514/263; 536/27.6; 536/26.13
[58] Field of Search ................ 514/300, 45, 46, 514/263; 536/27.6, 26.13

[56] References Cited

U.S. PATENT DOCUMENTS

| | | | |
|---|---|---|---|
| 4,673,563 | 6/1987 | Berne et al. | |
| 4,880,783 | 11/1989 | Mentzer, Jr. et al. | |
| 5,047,534 | 9/1991 | Peet et al. | 544/267 |
| 5,075,290 | 12/1991 | Findley et al. | |
| 5,206,222 | 4/1993 | Forman et al. | 514/46 |
| 5,231,086 | 7/1993 | Sollevi | 514/46 |
| 5,236,908 | 8/1993 | Gruber et al. | 514/46 |

OTHER PUBLICATIONS

Feldman MD, et al., "Pharmacologic Evidence That Deficient Production of Cyclic Adenoisine Monophosphate May Be The Primary Cause of Contractile Dysfunction in End–Stage Heart Failure", 43rd Annual Meeting of the American Federation for Clinical Research, Washington, D.C., held May 2–5, 1986, Clinical Research, vol. 34, No. 2, Issued 1986. 297A (Abstract Only).

Takeo et al., "Adenine Nucleotide Metabolites are Beneficial for Recovery of Cardiac Contractile Force After Hypoxia", J. of Molecular & Cellular Cardiology, 20 (3), Issued Mar. 1988, pp. 187–199 (abstract).

Belardinelli et al., "The cardiac effects of adenoisine," Progress Cardiovasc. Disease 32:73–97 (1989).

Belardinelli et al., "Actions of adenosine and isoproterenol on isolated mammalian ventricular myocytes," Circ. Res. 53:287–297 (1983).

Dobson et al., "The antiadrenergic actions of adenosine in the heart," In: Topics and Perspectives in Adenosine Research, Gerlach, E., Becker, B. F. (eds), Springer–Verlag, Berlin pp. 356–368 (1987).

Dobson et al., "Increased myocardial adenosine production and reduction of β–adrenergic contractile response in aged hearts," Circ. Res. 66:1381–1390 (1990).

Dobson, et al. "Adenosine A2–receptor agonists elicit a positive inotropic response and increase adenylyl cyclase activity in rat ventricular myocytes," Drug Develop. Res. 31:265 (abstract) (1994).

Dobson et al., "Role of extracellular and intracellular adenosine in the attenuation of catecholamine evoked responses in guinea pig heart," J. Mol. Cell. Cardiol. 16:813–822 (1984).

Dobson et al., "Endogenous adenosine inhibits catecholamine contractile responses in normoxic hearts," Amer. J. Physiol. 251:H455–H462 (1986).

Dobson et al., "Adenosine inhibition of β–adrenergic induced responses in aged hearts," Amer. J. Physiol. 265:H494–H503 (1993).

(List continued on next page.)

Primary Examiner—John C. Bleutge
Assistant Examiner—Robert H. Harrison
Attorney, Agent, or Firm—Fish & Richardson P.C.

[57] ABSTRACT

Disclosed are methods of increasing the contractile performance of a compromised myocardium in a mammal. The methods include administering a therapeutically affective amount of an adenosine $A_2$ receptor agonist. Also disclosed are methods that include administering in conjunction with an adenosine $A_2$ receptor agonist a second compound which potentiates the beneficial effect of the adenosine $A_2$ receptor agonist, e.g., an adenosine transport inhibitor, an inhibitor of adenosine metabolism or an adenosine $A_1$ receptor antagonist.

21 Claims, 11 Drawing Sheets

OTHER PUBLICATIONS

Fedida, "Modulation of cardiac contractility by α1–Adrenoceptor activity regulates release of adenosine from the ischemic myocardium in dogs," *Circ. Res.* 60:631–639 (1987).

Fenton et al., "Measurement by fluorescence of interstitial adenosine levels in normoxic, hypoxic, and ischemic perfused rat hearts," *Circ. Res.* 60:177–184 (1987).

Fenton et al., "Hypoxia enhances isoproterenol–induced increase in heart interstitial adenosine, depressing β–adrenergic contractile responses," *Circ. Res.* 72:571–578.

Fenton et al., "Effect of adenosine pretreatment on reperfusion contractile depression and arrhythmias in the low–flow ischemic β–adrenergic stimulated heart," *Drug Develop. Res.* 31:268 (abstract) (1994).

Gerencer, et al., "Cardiovascular selectivity of adenosine receptor agonists in anaesthetized dogs," *Br. J. Pharmacol.* 107:1048–1056.

Lai et al., "Negative dromotropism of adenosine under beta–adrenergic stimulation with isoproterenol," *Amer. J. Cardiol.* 70:1427–1431 (1992).

Olsson et al., "Cardiovascular Purinoceptors," *Physiological. Rev.* 70:761–845 (1990).

Romano et al., "Adenoosine receptor coupling of adenylate cyclase of rate ventricular myocyte membranes," *Am. J. Physiol.* 257:H1088–H1095 (1989).

Romano et al., "Adenosine attenuation of catecholamine–enhanced contractility of rat heart in vivo," *Amer. J. Physiol.* 260:H1635–H1639 (1991).

Sato et al., "Endogenous adenosine blunts β–adrenoceptor–mediated inotropic response in hypoperfused canine myocardium," *Circulation* 85:1594–1603 (1992).

Wilken et al., "Evidence against the presence of A2 adenosine receptors on guinea pig ventricular myocytes," *Eur. J. Pharmacol.* 192:161–163 (1991).

Xu, et al., "Expression and pharmacological characterization of a stimulatory subtype of adenosine receptor in fetal chick ventricular myocytes," *Circ. Res.* 70:56–65 (1992).

Zucchi, et al., "Cardiac A2 adenosine receptors—influence of ischemia," *Cardiovasc. Res.* 26:549–554 (1992).

Liang et al., "Adensine $A_{2a}$ and $A_{2b}$ Receptors in Cultured Fetal Chick Heart Cells," *Circulation Res.* 76:242–251 (1995).

1

ADENOSINE AS A POSITIVE INOTROP IN THE COMPROMISED HEART

STATEMENT AS TO FEDERALLY SPONSORED RESEARCH

Work on this invention was supported, in part, with funds from the United States government (Public Health Service Grants HL-22828, AG-11491 and HL-36964). The government therefore has certain rights in the invention.

FIELD OF THE INVENTION

This invention relates to methods of cardiac treatment.

BACKGROUND OF THE INVENTION

The binding of catecholamines, e.g., epinephrine or norepinephrine, to β-adrenergic cell surface receptors ("adrenoceptors") in the heart increases cardiac contractile and metabolic activity. The β-adrenoceptor-mediated cardiac stimulation involves a chain of events that includes binding of the catecholamine to the receptor, adenylyl cyclase activation, increased adenosine 3',5'-monophosphate (cAMP) formation, protein kinase activation, and action by phosphorylated proteins. In the heart, adenosine counteracts the β-adrenergic stimulation of adenylyl cyclase activity, thereby counteracting β-adrenoceptor-mediated cardiac stimulation. These negative regulatory effects of adenosine have been called the "antiadrenergic" actions of adenosine. (They have also been called the "indirect inhibitory" and "retaliatory" actions of adenosine.)

The antiadrenergic actions of adenosine on the heart are mediated by type $A_1$ adenosine receptors, which, like β-adrenergic receptors, are cell surface receptors. Type $A_1$ adenosine receptors have a high affinity for adenosine. Accordingly, the antiadrenergic actions of adenosine in the heart occur at relative low interstitial (i.e. extracellular) adenosine concentrations, i.e., 0.1–10 µM. Adenosine administered to the heart, at these low concentrations, in the absence of β-adrenergic stimulation, has no detectable direct effect on the above-mentioned metabolic and mechanical parameters.

A second type of cell surface receptor for interstitial adenosine, designated $A_2$, has a lower affinity for adenosine, i.e., approximately two to three orders of magnitude lower than the adenosine affinity of $A_1$ receptors. Type $A_2$ adenosine receptors exist in various mammalian tissues and have been detected in mammalian ventricular myocytes.

SUMMARY OF THE INVENTION

We have discovered that activating adenosine $A_2$ receptors in a mechanically compromised mammalian heart causes an increase in the contractile performance of the heart.

Accordingly, the invention features a method for increasing the contractile performance of a compromised myocardium in a mammal, comprising administering a therapeutically effective amount of an adenosine $A_2$ receptor agonist to said mammal. The adenosine receptor agonist used in the practice of this invention may be adenosine or any other compound that binds specifically to adenosine receptors, including $A_2$ receptors, and thereby causes the signal transduction normally caused by the binding of adenosine to the receptors. If the adenosine receptor agonist used is a compound other than adenosine, preferably it is a compound that is selective for adenosine $A_2$ receptors.

A second compound which potentiates the beneficial effect of adenosine may be administered to a mammal, in conjunction with adenosine or an adenosine receptor agonist. The beneficial effects of adenosine could be potentiated in at least two ways: (1) by enhancing the interstitial concentration of adenosine in the myocardium; and (2) inhibiting the $A_1$ receptor-mediated antiadrenergic effects of adenosine.

One means whereby the second compound could enhance the interstitial concentration of adenosine is inhibition of the clearance (i.e., removal) of interstitial adenosine. More particularly, clearance of interstitial adenosine is inhibited by administering an adenosine transport inhibitor in conjunction with adenosine or an adenosine receptor agonist. Another means whereby the second compound could enhance the interstitial concentration of adenosine is the inhibition of adenosine metabolism.

The $A_1$ receptor-mediated antiadrenergic effects of adenosine are inhibited by administering an $A_1$ receptor antagonist, i.e., a compound that binds specifically to $A_1$ receptors and "blocks" them without causing signal transduction.

The positive inotropic response of a mammalian heart resulting from adenosine $A_2$ receptor activation is relatively small, as compared to the β-adrenergic receptor-mediated response resulting from catecholamine stimulation. The moderate increase in the contractile performance of a compromised mammalian heart achieved according to the present invention advantageously avoids overstimulation and concomitant heart failure, which may result from more potent inotropes.

As used herein, "adenosine $A_2$ receptor agonist" means adenosine or any other compound that binds specifically to adenosine receptors, including $A_2$ receptors, and thereby causes the $A_2$ receptor-mediated signal transduction normally caused by the binding of adenosine to the $A_2$ receptors.

As used herein, "adenosine receptor antagonist" means a compound that binds specifically to one or more types of adenosine receptor without causing the signal transduction normally caused by the binding of adenosine to the receptor(s). A particular compound may be an antagonist for adenosine $A_1$ receptors, $A_2$ receptors, or both.

As used herein, "compromised myocardium" means a myocardium whose mechanical performance, in terms of an accepted parameter, is at least 10% below that which is normal for an individual of similar size and age, as measured under resting conditions or exercise conditions.

As used herein, in the context of an isolated myocyte, "contractile performance" means any of the following: length change or shortening ("LC"), duration of shortening ("DS"), time to peak shortening ("TPS"), maximal rate of shortening ($+dL/dt_{max}$), time to 75% relaxation ("TR"), or maximal rate of relengthening ($-dL/dt_{max}$).

As used herein, in the context of an intact heart, "contractile performance" means any of the following: stroke volume, left ventricular pressure ("LVP") change, time to peak pressure, maximal rate of pressure increase ($+dP/dt_{max}$), time to 75% relaxation, or maximal rate of pressure decrease ($-dP/dt_{max}$).

As used herein, "hypoxic" means arterial blood oxygen saturation of 90% or lower, with normal arterial blood oxygen saturation being 95%.

As used herein, "inotropic" means influencing the contractility of muscular tissue.

As used herein, "ischemic" means having a blood flow at least 10% below that which is normal for an individual of similar size and age, as measured under resting conditions or exercise conditions. In an adult human, normal resting blood flow is approximately 1 ml/min/gram of myocardial mass. During exercise, blood flow typically rises to approximately 3–6 ml/min/gram of myocardial mass.

As used herein, a "therapeutically effective amount" of adenosine or an adenosine receptor agonist is an amount that causes an increase of at least 10% in stroke volume, LVP, or maximal rate of pressure increase (+dP/dt$_{max}$) in the mammal to which it is administered.

Other features and advantages of this invention will be apparent from the following description of the preferred embodiments thereof, and from the claims.

DETAILED DESCRIPTION

Figure 1:
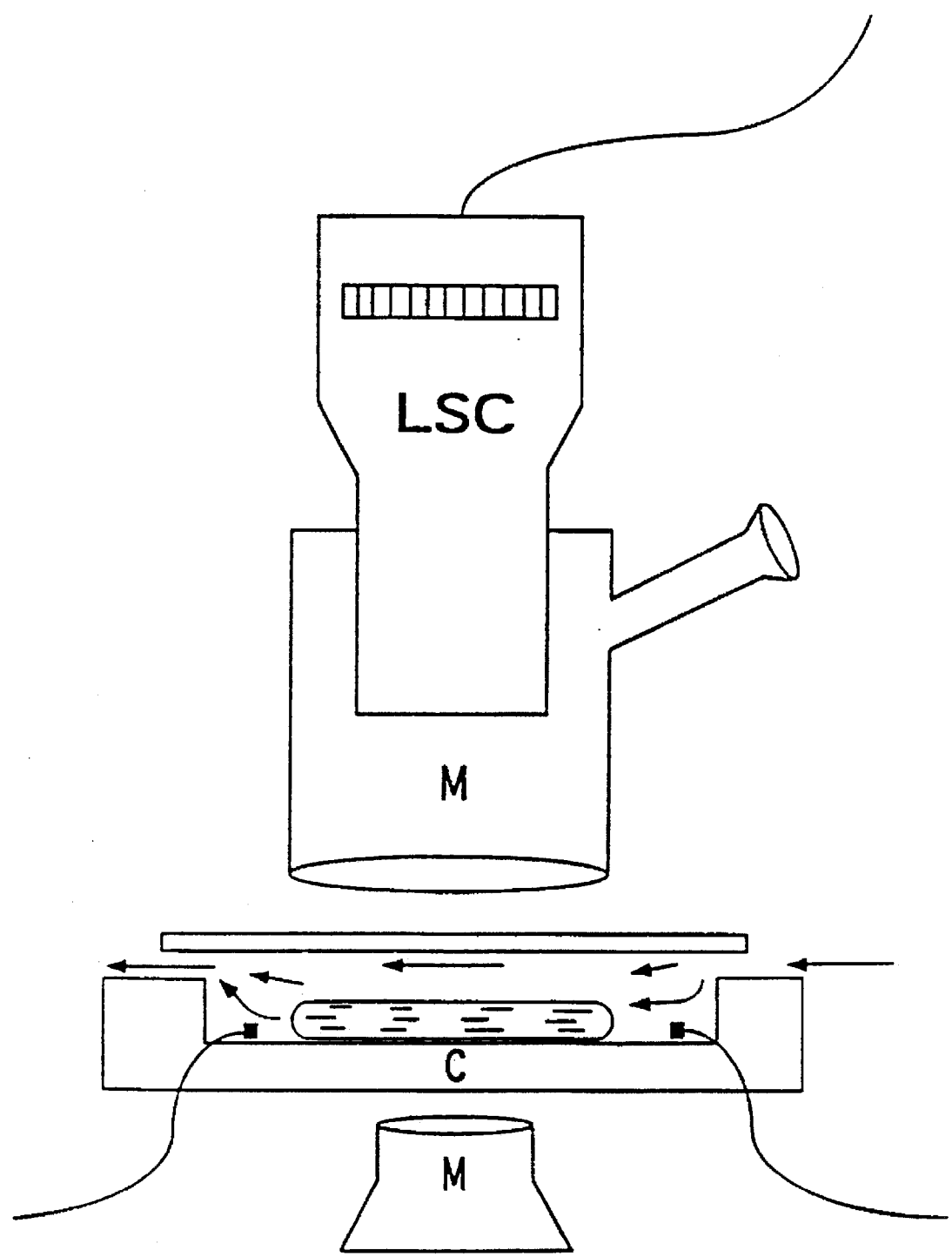
FIG. 1 is a schematic diagram of the instruments used to obtain contractile information from single rat heart ventricular myocytes. Myocytes were continuously suffused in a myocyte chamber (C) from right to left with suffusion solution. Platinum wire electrodes in the base of the chamber were used to elicit myocyte contractions at 0.5 Hz. The bottom and top of the chamber are glass, so that when mounted on an inverted microscope (M), contractions could be visualized. A line scan camera (LSC) fixed to the inverted microscope was used to record the shortening of single ventricular myocytes associated with each contraction.

This invention provides a simple, rapid and efficacious method for increasing the contractile performance of a compromised myocardium. The compromise may result from various factors, e.g., ischemia, hypoxia, hypertrophy, old age, underlying heart disease of unknown cause, or combinations thereof.

An adenosine receptor agonist, e.g., adenosine, can be used according to this invention to treat a mammal that has been identified as having a compromised myocardium. Mammals, and humans in particular, are known to display various signs and symptoms relating to the existence of a compromised myocardium. The recognition of such signs and symptoms is within the skill of medical practitioners. Signs and symptoms of a compromised myocardium in a human patient include, but are not limited to, the following: decrease in ejection fraction, as determined by echocardiography; increase in heart size, as determined by echocardiography or X-ray; increase in diastolic pressure; dyspnea; shortness of breath; and effusions around the heart, i.e., the accumulation of fluid in the pericardial cavity.

This invention involves activating type $A_2$ stimulatory adenosine receptors, which have a low affinity for adenosine. Therefore, the invention may be practiced with adenosine or any other compound that is an $A_2$ receptor agonist, i.e., that binds to the $A_2$ receptor, thereby causing signal transduction. The following compounds are examples of adenosine $A_2$ receptor agonists: adenosine, carboxyethyl-phenethyl-amino-ethylcarboxamido-adenosine ("CGS-21680"), N-ethyl-carboxamidoadenosine ("NECA"), naphthyl-substituted aralkoxyadenosine ("SHA-082"), and 2-phenylaminoadenosine.

The following considerations may be useful in identifying additional compounds that are adenosine $A_2$ receptor agonists. The introduction of an aromatic substituent at the amino group on the 6 position of the adenine moiety increases adenosine $A_2$ receptor selectivity (Bridges et al., *J. Med. Chem.* 31:1281 (1988)). A $C_2H_5$—N—R substituent at the 5' position plus a large aromatic substituent at the 2 position markedly increases selectivity for adenosine $A_2$ receptors (Hutchinson et al. *J. Pharmacol. Exp. Thera.* 251:47 (1989)). Also, 2-hexynyl 5'-ethyl-carboxamido additions enhance adenosine $A_2$ receptor agonist activity (Monopoli et al., *Arzneim.-Forsch Drug Res.* 44:1296 (1994)).

Although type $A_2$ receptors have a relatively low affinity for adenosine, they may, but will not necessarily, have a low affinity for a particular adenosine receptor agonist. An adenosine receptor agonist may display specificity for type $A_2$ receptors, or it may lack specificity, activating type $A_1$ receptors as well as type $A_2$ receptors. If the invention is practiced with adenosine or a non-specific adenosine receptor agonist, the level of adenosine or agonist in the myocardium must be sufficiently elevated to activate the type $A_2$ adenosine receptors. Insufficient elevation may activate type $A_1$ adenosine receptors only, thereby decreasing contractile performance of the heart.

In the practice of this invention, an adenosine $A_2$ receptor agonist, adenosine $A_1$ receptor antagonist, adenosine transport inhibitor, inhibitor of adenosine metabolism, or any combination thereof, may be administered by any route suitable for delivery to the myocardium. The preferred route of administration is intravenous. The adenosine or other adenosine receptor agonist may be comprised in any pharmaceutically acceptable composition. Preferably, intravenous adenosine is administered as a pharmaceutically acceptable aqueous solution. Preferably, adenosine is administered at a predetermined dose of between 1 and 140 µg/kg/min. More preferably, the predetermined adenosine dose is between 10 and 100 µg/kg/min. Most preferably, the predetermined adenosine dose is between 20 and 40 µg/kg/min. When the invention is practiced with adenosine, a selected combination of dose level and route of administration preferably yields a serum adenosine concentration between 10 nM and 10 mM. If adenosine or other adenosine receptor agonist is administered in conjunction with a second compound which potentiates the beneficial effect of those compounds, the dose level of adenosine or adenosine or the adenosine receptor agonist should be adjusted accordingly. It may be necessary to begin with a predetermined dose of adenosine or adenosine receptor agonist and then titrate the dosage according to one or more selected clinical parameters, in order to achieve the desired increase in contractile performance of the compromised myocardium. The dose level of an adenosine receptor agonist will depend on various factors, including the following: toxicity, in vivo half-life, affinity for the type $A_2$ adenosine receptor and affinity for the type $A_1$ adenosine receptor. The administration of an adenosine $A_2$ receptor agonist, adenosine $A_1$ receptor antagonist, adenosine transport inhibitor, inhibitor of adenosine metabolism, or any combination thereof, can be singular or intermittent, in response to acute signs or symptoms of myocardial compromise. Alternatively, the administration can be continuous, for an indefinite period, to sustain the performance of a chronically or permanently compromised myocardium.

When adenosine or other adenosine $A_2$ receptor agonist is administered according to this invention, it is desirable to monitor one or more of the compound's physiological effects. Such monitoring may be used, in a particular individual, to verify increased myocardial contractile performance, to identify undesirable side effects and, as noted above, to adjust the dose level. Examples of potential undesirable side effects associated with adenosine administration are flushing in the head and neck, "uneasy" feelings, and transient cardiac arrest due to A-V nodal blockade. Preferably the effects of adenosine or an adenosine receptor agonist on a patient would be assessed by monitoring one or more of the following: blood pressure, ease of patient's breathing, image of the heart produced by echocardiography (ultrasound cardiography), and electrical activity of the heart (electrocardiography).

Adenosine is normally present in micromolar amounts in the mammalian myocardium, where it is involved in a variety of physiological and biochemical processes. It is transported across biological membranes, e.g., into or out of cells or organelles, by adenosine transport proteins (also called "transporters" or "carriers"). One mechanism by which interstitial adenosine is cleared (i.e., removed) is transport into cells, where it is metabolized in various biochemical pathways. Therefore, high levels of exogenous interstitial adenosine may be promoted initially or prolonged, by administering, in conjunction with adenosine, a compound that inhibits adenosine transport into cells. Accordingly, in a preferred embodiment of this invention, an adenosine transport inhibitor is administered in conjunction with adenosine administration. Examples of adenosine transport inhibitors are dipyridamole, S(4-nitrobenzyl)-6-thioinosine, S(4-nitrobenzyl)-6-thioguanosine and Draflazine (see, Van Belle, *Drug Devel. Res.* 31:329, abstr. no. 1383 (1994). The adenosine transport inhibitor may be introduced into the mammal by any suitable method, including via an oral, transmucosal, intravenous, intramuscular or subcutaneous route. Alternatively, the transport inhibitor may be inhaled by the mammal.

Another approach to inhibiting the clearance of interstitial adenosine is the inhibition of adenosine metabolism. One pathway of adenosine metabolism is the conversion of adenosine to inosine by adenosine deaminase. Accordingly, in one embodiment of this invention, an adenosine deaminase inhibitor is administered in conjunction with adenosine administration. An example of an adenosine deaminase inhibitor is erythro-9-(2-hydroxy-3-nonyl) adenine ("EHNA"). Another pathway of adenosine metabolism is the conversion of adenosine to adenosine monophosphate by adenosine kinase. Accordingly, in another embodiment of this invention, an adenosine kinase inhibitor is administered in conjunction with adenosine administration. An example of an adenosine kinase inhibitor is iodotubercidin.

When adenosine is administered according to this invention, i.e, to increase the contractile performance of a compromised myocardium via its interaction with the type $A_2$ receptors, the adenosine may be simultaneously exerting a counterproductive effect via its interaction with the type $A_1$ receptors. Accordingly, in one embodiment of this invention, a selective inhibitor of $A_1$ receptor-mediated (antiadrenergic) adenosine effects, i.e., an $A_1$ receptor antagonist, is administered in conjunction with adenosine administration. The following compounds are examples of $A_1$ receptor antagonists: 1-allyl-3,7-dimethyl-8-phenylxanthine, 8-cyclopentyl-1,3-dimethylxanthine, 8-cyclopentyl-1,3-dipropylxanthine ("DPCPX"), 1,3-diethyl-8-phenylxanthine, 8-phenyltheophylline and xanthine amine congener ("XAC"). Similarly, an $A_1$ receptor antagonist can be administered in conjunction with an adenosine receptor agonist. This is particularly desirable if the adenosine receptor agonist is not specific for type $A_2$ adenosine receptors.

Chemical compounds useful in practicing this invention or used in the experiments described below are often known in the art primarily by abbreviations, common names or arbitrary designations, several of which are collected in Table 1.

TABLE 1

NOMENCLATURE AND ACTIVITY OF SELECTED AGONISTS AND ANTAGONISTS

| ABBREVIATION/ COMMON NAME | CHEMICAL COMPOUND | RECEPTOR/ ACTIVITY |
|---|---|---|
| CGS-21680 | 2-p-(2-carboxy-ethyl) phenethyl-amino-5'-N-ethylcarboxamido-adenosine | $A_2$ agonist |
| CGS-15943 | 9-chloro-2-(2-furanyl)-5,6-dihydro-1,2,4-triazolo-(1,5-C)quinazolin-5-imine | $A_2$ antagonist |
| CSC | 8-(3-chlorostyryl)caffeine | $A_2$ antagonist |
| DMPX | 3,7-dimethyl-1-(2-propargyl)xanthine | $A_2$ antagonist |
| DPCPX | 1,3-dipropyl-8-cyclopentylxanthine | $A_2$ antagonist |
| NECA | N-ethylcarboxamido-adenosine | $A_2$ agonist |
| ISO | Isoproterenol | $\beta$-adrenergic agonist |
| SHA-082 | naphthyl-substituted aralkoxyadenosine | $A_2$ agonist |
| PIA | phenylisopropyladenosine | $A_1$ agonist |

EXPERIMETNAL INFORMATION

Ventricular Myocyte Study

Primary cultures of adult rat ventricular myocytes were prepared essentially according to previously described methods (Romano et al., *Am. J. Physiol.* 257:H1088 (1989)). Two male Sprague-Dawley rats (Charles River, Wilmington, Mass. or Harlan, Indianapolis, Ind.) were decapitated, and the hearts were rapidly excised and constant pressure (70 cm $H_2$) and nonrecirculated) perfused for 10 minutes through the aortas with filtered (0.45 µm membrane filter) perfusing solution (NaCl, 118 mM; glucose, 10 mM; $NaHCO_3$ 25 mM; KCl, 4.69 mM; $MgSO_4$ 1.18 mM; and $KH_2PO_4$, 1.18 mM; (pH 7.4)), to which 2.5 Mm $CaCl_{12}$ was added, at 37° C. After equilibration, the hearts were constant pressure perfused with fresh physiological saline ("PS") containing no added $Ca^{2+}$ until spontaneous contractions ceased (i.e., ~30 seconds). The hearts were then perfused for 4–10 minutes in a nonrecirculating manner with PS containing 0.73 mg/ml collagenase, 0.16 mg/ml hyaluronidase, 1 mg/ml recrystallized bovine serum albumin ("BSA") and 48.4 µM $Ca^{2+}$ at a rate of 3–4 ml/min/heart. Ventricles, free of atria, were removed from the perfusion system, cut into 8 pieces and placed in a 50 ml Erlenmeyer flask with 5 ml of PS containing 0.73 mg/ml collagenase, 0.16 mg/ml hyaluronidase, 2.5 mg/ml BSA, and 50 µM $Ca^{2+}$ (incubation solution). The flask was gently shaken (40 cycles/min) in a reciprocating water bath with continuous gassing (95% $O_2$, 5% $CO_2$) for 7 minutes at 37° C. The incubation solution was aspirated and this shaking procedure was repeated with fresh incubation solution 3–5 times depending on the likelihood that the tissue was ready to dissociate. After the final incubation period, the solution was aspirated and replaced with 10 ml of fresh incubation solution. The flask was then shaken rapidly (120 cycles/min) for 10 minutes with gassing to dissociate the myocytes. The flask contents were filtered through a 250 µm nylon mesh into a 50 ml polypropylene centrifuge tube, to which 40 ml of PS containing 5.95 mg/ml BSA and 99.7 µm $Ca^{2+}$ (wash solution) was gradually added.

The myocytes were allowed to settle for 15 minutes, and the upper two thirds of the wash solution was aspirated. Upon the addition of 30–35 ml of wash solution, this settling step was repeated. The wash solution was aspirated and the myocyte pellet was resuspended in 10 ml of minimum essential medium ("MEM"). The myocyte suspension was allowed to settle for 5 minutes and then brought to a final volume of 22 ml with MEM. Two milliliters of the myocyte suspension was seeded onto each of 60 mm culture dishes containing 2 ml of MEM. Because myocytes do not attach under these plating conditions, these myocytes were used for contractile experiments.

When myocytes were to be used for biochemical studies, each of the culture dishes was preincubated for 2 hours with 1 ml of MEM containing 33 µg of laminin in a 37° C. incubator gassed with 5% $CO_2$ in room air. The laminin solution was removed prior to myocyte seeding. After seeding, the dishes were incubated for an additional 2 hours. The settling and short term culture procedures were performed to purify the myocytes so that >95% of the myocytes adhering to the dishes were rod shaped.

The contractile function of individual myocytes was assessed by dispersing 50–100 cells in a 506 µl myocyte chamber (11×23×2 mm deep). The chamber (FIG. 1) was continuously suffused (850 µl/min) with fresh suffusion solution ("SS") in mM: 136.4 NaCl, 4.7 KCl, 1.0 $CaCl_2$, 10 hydroxyethylpiperzine-ethanesulfonicacid (HEPES), 1.0 $NaHCO_3$, 1.2 $MgSO_4$, 1.2 $KH_2PO_4$, 10 glucose, 0.6 ascorbate, 1.0 pyruvate) at 20° C. The chamber was mounted on an inverted microscope stage and contained platinum wire electrodes for initiating myocyte contraction at 0.5 Hz (voltage 10% above threshold for 5 msec duration).

Figure 2A:
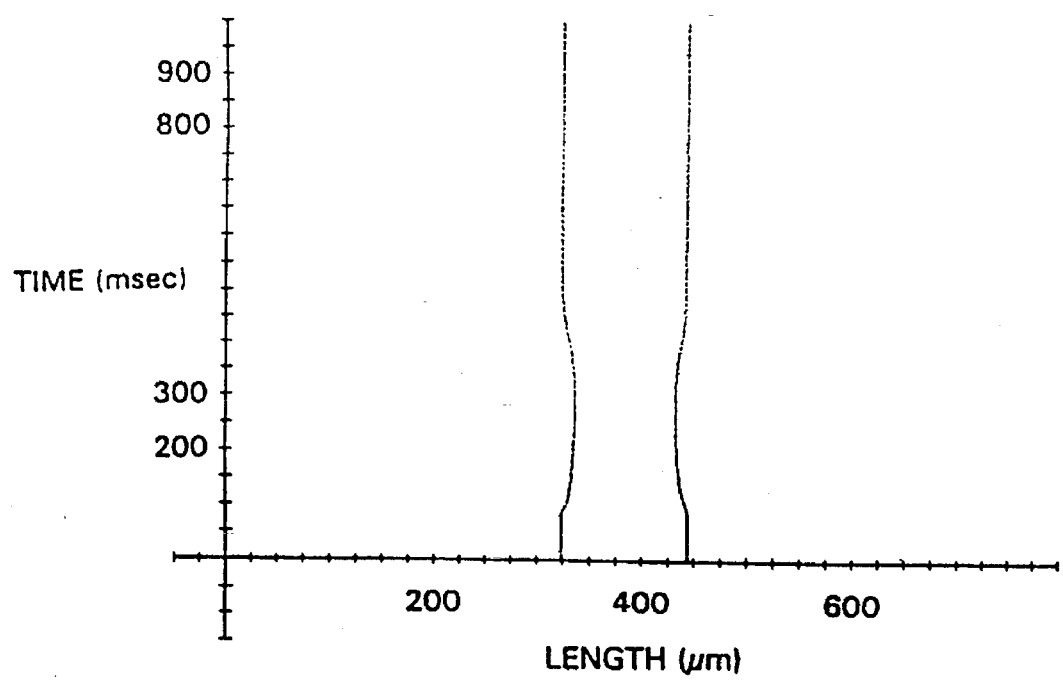
FIGS. 2A–2D are graphs, generated on a computer screen, illustrating the raw data in pixels indicating edge detection (length) collected over 1 sec (FIG. 2A), myocyte length vs. time (FIG. 2B), myocyte length change (Δlength or LC) vs. time (FIG. 2C) and + and −dL/dt vs. time (FIG. 2D) for a single rat ventricular myocyte contraction. Time and monocyte length are in msec and microns (μm), respectively.
Figure 2B:
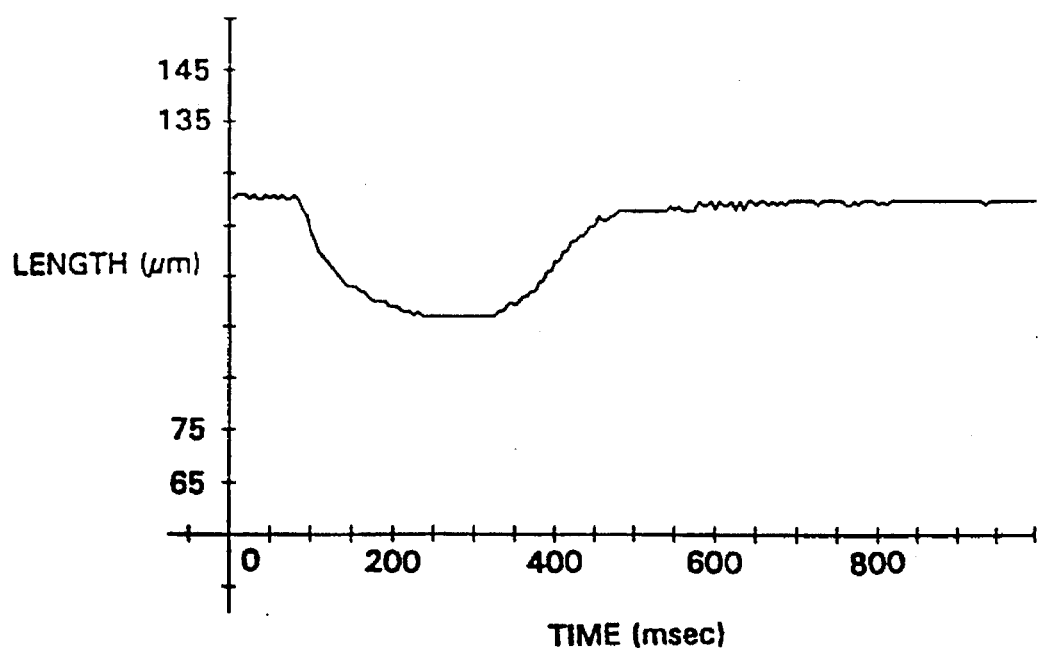
Figure 2C:
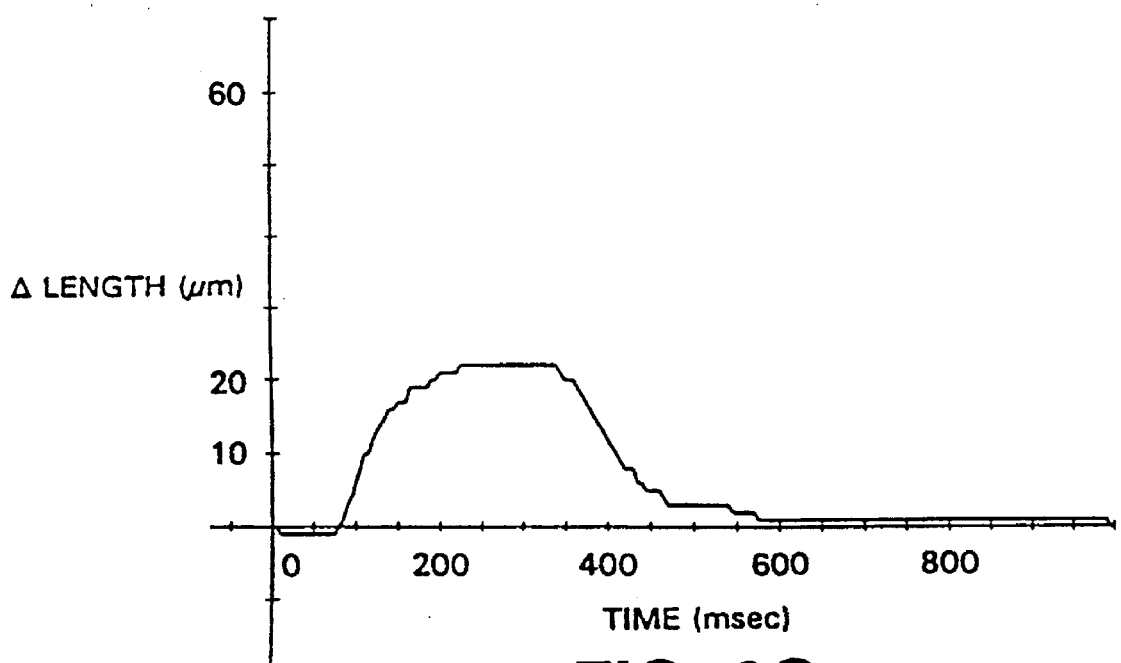
Figure 2D:
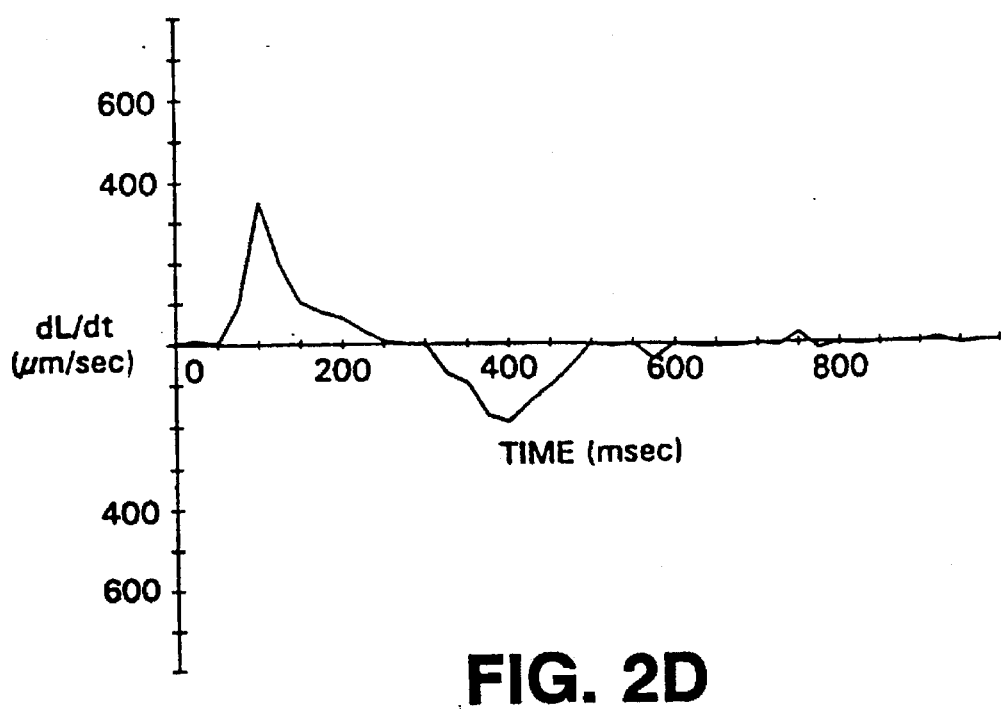

The image of the myocyte was projected via an inverted microscope at 300× onto a line scan camera (Fairchild, Model 1600R) containing a linear array (1×3456) of photodiodes. When aligned with the longitudinal axis of the cell the camera detected the movement of the 2 ends of the myocyte upon contraction (shortening and relengthening). The signals from the line scan camera were displayed on an oscilloscope (Hitachi, Model V-660) which permitted optimal positioning of the camera over the myocyte. When the myocyte was transilluminated, both ends of the cell were easily discriminated. Myocyte length and length change with respect to time for a single contraction was measured by determining the pixels in which the appropriate transitions between light and dark occurred. The line scan camera was calibrated with a stage micrometer scaled in 10 µm divisions. The signals from the camera were directed to a Hewlett Packard computer (Model Vectra RS/20C). Custom computer programming (MCS Computer Consulting, Keene N.H.) permitted determination of myocyte length (L), maximum length change (shortening) with contraction ("LC"), duration of shortening (DS), time-to-peak shortening ("TPS"), time to 75% relaxation (relengthening, "TR") and the rate of maximal shortening ($+dL/dt_{max}$) and relaxation ($-dL/dt_{max}$). An example of edge movement detection for a single contraction of a myocyte is shown in FIG. 2A. Also illustrated as a function of time is L, ΔL and + and $-dL/dt$ in FIGS. 2B, 2C, and 2D, respectively.

After a 3–4 hour incubation period, myocytes were harvested by placing the culture dishes on ice; aspirating and discarding the culture medium; scraping the attached cells into 1 ml of ice cold buffer (pH 7.4) containing 10 mM HEPES and 1 mM dithiothreitol (DTT); and transferring the mixture to a 40 ml centrifuge tube. The culture dishes were rinsed twice with buffer, and the rinses were added to the centrifuge tube. The myocytes were centrifuged at 45,000 × g for 45 minutes and the supernatant was discarded. The pellet was resuspended in 40 mM HEPES (pH 7.4) to yield 3.5–4 mg protein/ml and homogenized with a small clearance Dounce tissue grinder (8 strokes). The membranes were centrifugated as described above, resuspended (3–4 mg protein/ml) in 40 mM HEPES (pH 7.4), and assayed for adenylyl cyclase activity immediately or stored at −80° C. and assayed within 10 days.

Crude ventricular myocardial membranes were prepared according to the following procedure. Isolated rat hearts were perfused with 5 ml of ice cold saline (0.9% NaCl) to wash out the blood, minced into 2–3 $mm^3$ cubes, and placed in 10 ml of homogenization buffer (HB) containing 10 mM HEPES (pH 7.4), 1 mM ethylenediamine-tetraacetic acid (EDTA), 1 mM DTT and 10 µg/ml soybean trypsin inhibitor. The suspension was homogenized with a PT-10 Polytron™ generator at a speed of 6 for two 15-second periods separated by 15 seconds. The homogenized material was also treated with 2 strokes of a glass/teflon motor driven Potter-Elvehjen homogenizer operated at ½ full speed. Upon addition of 4.7 ml of HB containing 1.25M sucrose the homogenate was mixed and centrifugated at 1,000 × g for 15 minutes. The supernatant was filtered through 4 layers of cheesecloth and 14.5 ml HB was added. The mixture was centrifugated at 45,000 × g for 45 minutes and the pellet was suspended in 3–5 ml of 40 mM HEPES buffer (pH 7.4) with the small clearance Dounce tissue grinder (6 strokes) to yield 3–5 mg protein/ml. Membranes were assayed immediately for adenylyl cyclase activity. All preparative steps for the crude membranes were performed at 0°–1° C.

Protein concentration was determined by a standard method (BCA Protein Assay, Pierce, Rockford, Ill.) using BSA as a standard. Each 60 mm culture dish contained 200–600 µg of adhering rod shaped myocyte protein resulting in a total of 3–6 mg of protein from a pair of hearts.

The assay system used to measure adenylyl cyclase activity minimizes the formation of endogenous adenosine. The assay used was essentially as described by Romano et al. (supra). Myocyte membranes (15–25 µg protein) were incubated in 50 µl of a buffer containing 40 mM HEPES (pH 7.4), 5 mM $MgCl_2$, 1 mM DTT, 5.5 mM KCl, 0.1 mM 2'-deoxy-cAMP (dcAMP), 0.1 mM 2'-deoxy ATP (dATP), 20 mM phosphoenolpyruvate, 2 units pyruvate kinase, 0.25 units adenosine deaminase, 1 mM ascorbic acid, 100 mM NaCl, 0.1 mM ethyleneglycol-bis (β-aminoethylether) N,N, N',N',-tetroaceticacid (EGTA), 10 µM guanosine 5'-triphosphate (GTP), and ~2×10$^6$ counts/minutes of [α-$^{32}$P]dATP for 20 minutes at 30° C. The reaction was stopped by adding 40 µl of a solution containing 2% sodium dodecyl sulfate (SDS), 45 mM ATP, 1.3 mM cAMP, and [$^3$H]dcAMP (~4000 count/min) and by boiling for 2 minutes. The formed [α-$^{32}$P]dcAMP was separated from the [α-$^{32}$P]dATP by sequential chromatography using columns of cation exchange resin AG 50W-X4 (200–400 mesh) and neutral alumnia AG 7 (100–200 mesh) after the methods of Salomon (*Adv. Cyclic Nucleotide Res.* 10:35 (1979). All results were corrected for column recovery of [$^3$H]dcAMP, which ranged between 60 and 90%. The activity of the adenylyl cyclase is expressed as pmol [α-$^{32}$P]dcAMP formed/min/mg protein.

Cyclic AMP levels were determined in cultures of ventricular myocytes according to the following method. After the 2-hour incubation period, the MEM was aspirated and replaced with 2 ml of fresh MEM. Adenosine agonists, ISO, or adenosine antagonists were added to the medium bathing the cells at the concentrations and times indicated. The experiment was terminated by removing the medium from the dish and adding 200 µl of 1N HCl over the cultured myocyte surface. The dishes were then frozen in liquid $N_2$ and stored at −70° C. or held on ice momentarily until extraction was initiated.

For assay, the contents of the dishes were transferred (using 1 ml of distilled/deionized $H_2O$) into microcentrifuge tubes. The extracts were heated for 1 hour at 57° C. and sonicated for 10 minutes. The extracts were then centrifugated at 14,000 x g for 15 minutes. The supernatant was removed, evaporated, reconstituted in 500 µl of 50 mM sodium acetate buffer and assayed for cAMP using an $^{125}$I-cAMP RIA kit (Amersham). The pellet was solubilized with 0.1N NaOH and protein determined. The cAMP values are reported in pmol cAMP/mg protein of the extract pellet (total cell protein). This cAMP assay procedure routinely provided recovery values in excess of 90%.

All data are expressed as means±one standard error of the mean (SE). The concentration of agonist that produced 50% of the maximum stimulatory response ($EC_{50}$) was determined from nonlinear regression analysis. Statistical analysis was performed on actual (not normalized) data. Statistical significance was determined using one-way independent analysis of variance. A probability (P value) of less than 0.05 was accepted as a statistically significant difference.

Ventricular Myocyte Results

Figure 3:
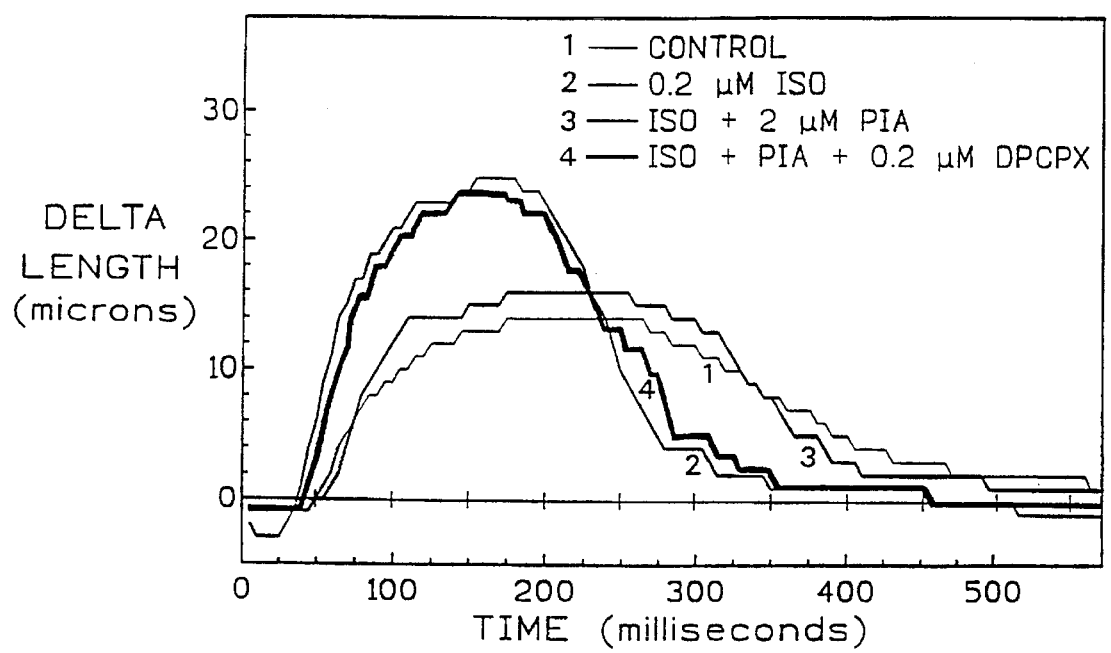
FIG. 3 is a graph illustrating the effect of isoproterenol ("ISO"), phenylisopropyladenosine ("PIA"), and 1,3-dipropyl-8-cyclopentylxanthine ("DPCPX") on ventricular myocyte contraction. Traces are length changes associated with single contractile shortenings of a representative rat ventricular myocyte upon the sequential addition every 8–10 min of 0.2 μM ISO, ISO+2 μM PIA, and ISO+PIA+0.2 μM DPCPX.

An adenosine $A_1$ receptor agonist, phenylisopropyladenosine ("PIA"), reduced β-adrenoceptor-mediated increases in ventricular myocyte contractility, caused by isoproterenol. The $A_1$ receptor-mediated inhibition of β-adrenoceptor-mediated increases in contractility was reduced by an adenosine $A_1$ receptor antagonist. In individual contracting rat ventricular myocytes ISO at 0.2 µM increased by 61, 63 and 100% the maximum length change (shortening) with contraction (LC) and maximum rates of shortening (+dL/dt$_{max}$) and relaxation (−dL/dt$_{max}$), respectively (Table 2). These increases were accompanied by decreases of 30, 14 and 39% in the duration of shortening ("DS"), time-to-peak shortening ("TPS") and time to 75% relaxation ("TR"), respectively. A typical recording depicting the length changes associated with individual myocyte contractions under these conditions is given in FIG. 3. An adenosine $A_1$ receptor agonist, PIA, at 2 µM reduced the ISO-induced increases or decreases in LC, DS, TPS, TR, +dL/dt$_{max}$ and −dL/dt$_{max}$ by 91, 47, 82, 37, 60 and 78%, respectively. An adenosine $A_1$ receptor antagonist, DPCPX, at 0.2 µM reversed the PIA reduction of the ISO induced contractile responses.

DPCPX. After the control values were obtained, the three combinations, ISO alone, ISO+PIA, ISO+PIA+DPCPX were added sequentially every 8–10 min and the maximum responses recorded. Asterisks denote a statistically significant difference from the appropriate control value. Daggers denote a statistically significant difference from the corresponding ISO value. Double daggers denote a statistically significant difference from the corresponding ISO+PIA value.

Figure 4:
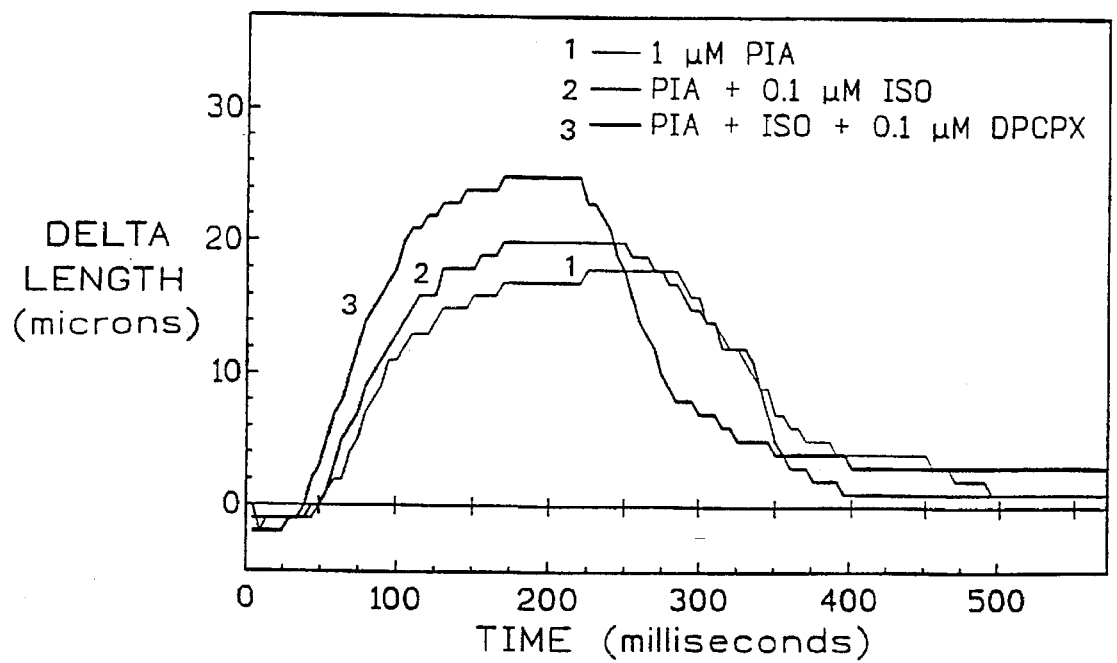
FIG. 4 is a graph illustrating the effect of ISO and DPCPX on ventricular myocyte contraction in the presence of PIA. Traces are length changes associated with single contractile shortenings of a representative rat ventricular myocyte in the presence of 1 μM PIA with sequential addition every 8–10 min of 0.1 μM ISO, and ISO +0.1 μM DPCPX.

In the presence of the adenosine $A_1$ receptor agonist, PIA, the β-adrenoceptor-mediated positive inotropic response in ventricular myocytes (elicited by ISO) was enhanced by an adenosine $A_1$ receptor antagonist, DPCPX. PIA at 1 µM had no effect on ventricular myocyte contractile variables (Table 3). In the presence of PIA, ISO at 0.1 µM increased LC, +dL/dt$_{max}$ and −dL/dt$_{max}$ by 44, 70, 93%, respectively, and decreased TR by 10%. Typical recordings of length changes associated with contractions from a single ventricular myocyte under these conditions is illustrated in FIG. 4. The addition of 0.1 µM DPCPX resulted in a further increase of the ISO induced enhancement in LC by 26% and +dL/dt$_{max}$ by 40%. The DPCPX also lowered the ISO induced decrease in DS by 27% below that observed in the presence of PIA+ISO.

TABLE 2

REDUCTION BY PIA OF ISO-ELICITED CONTRACTILE
RESPONSES OF VENTRICULAR MYOCTYES REVERSED BY DPCPX.

|  | LC (µm) | DS (msec) | TPS (msec) | TR (msec) | +dL/dt$_{max}$ (µm/msec) | −dL/dt$_{max}$ (µm/msec) |
| --- | --- | --- | --- | --- | --- | --- |
| CONTROL | 18 ± 2 | 375 ± 18 | 120 ± 3 | 345 ± 10 | 160 ± 14 | 90 ± 12 |
| ISO | 29 ± 2* | 263 ± 16* | 103 ± 4* | 210 ± 8* | 260 ± 13* | 180 ± 17* |
| ISO + PIA | 19 ± 2† | 316 ± 17† | 117 ± 4† | 260 ± 9† | 200 ± 15† | 110 ± 18† |
| ISO + PIA + DPCPX | 26 ± 2‡ | 268 ± 14‡ | 102 ± 3‡ | 185 ± 11‡ | 245 ± 12‡ | 165 ± 16‡ |

Values are mean ± SE (N = 6).

In the experiment summarized in Table 2, the myocyte suffusion contained 0.2 µM ISO, 2 µM PIA and 0.2 µM

TABLE 3

ANTAGONISM BY DPCPX OF PIA REDUCTION OF ISO-ELICITED VENTRICULAR MYOCYTE CONTRACTILE RESPONSES

|  | LC (μm) | DS (msec) | TPS (msec) | TR (msec) | +dL/dt$_{max}$ (μm/msec) | −dL/dt$_{max}$ (μm/msec) |
|---|---|---|---|---|---|---|
| CONTROL | 16 ± 2 | 380 ± 19 | 152 ± 4 | 307 ± 9 | 116 ± 15 | 87 ± 20 |
| ISO | 16 ± 2 | 374 ± 23 | 153 ± 5 | 308 ± 8 | 115 ± 17 | 85 ± 21 |
| ISO + PIA | 23 ± 2* | 319 ± 22 | 146 ± 6 | 278 ± 7* | 196 ± 21* | 164 ± 16* |
| ISO + PIA + DPCPX | 29 ± 2*† | 233 ± 21*† | 143 ± 8 | 273 ± 5* | 275 ± 25*† | 195 ± 19* |

Values are mean ± SE (N = 6).

In the experiment summarized in Table 3, the myocyte suffusion contained 1 μM PIA, 0.1 μM ISO, and 0.1 μM DPCPX. After the control values were obtained, the three combinations, PIA alone, PIA+ISO, and PIA+ISO+DPCPX were added sequentially every 8–10 min and the maximum responses recorded. Asterisks denote a statistically significant difference from the comparable control and PIA values. Daggers denote a statistically significant difference from the comparable PIA+ISO value.

Figure 5:
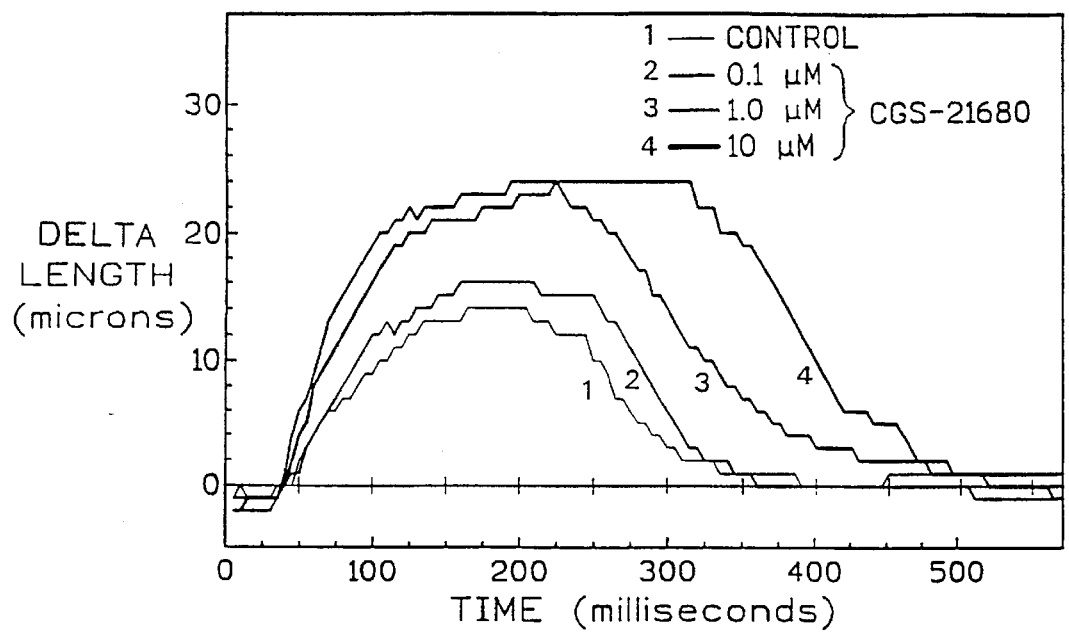
FIG. 5 is a graph illustrating the effect of 2-p-(2-carboxyethyl)phenethyl-amino-5'-N-ethylcarboxamido-adenosine ("CGS-21680") on ventricular myocyte contraction. Traces are length changes associated with single contractile shortenings of a representative rat ventricular myocyte upon sequential addition of increasing concentrations of CGS-21680 (0.1 to 10 μM) every 10 min.

The adenosine A$_2$ receptor agonist, CGS-21680, caused a concentration-dependent increase in ventricular myocyte contractility. CGS-21680 at 0.01 μM increased TPS by 11% and TR by 12% (Table 4). At 0.1 μM the agonist caused 28, 32, 30, 22 and 27% increases in LC, DS, TPS, TR and +dL/dt$_{max}$, respectively. A typical recording illustrating length changes associated with contractions of a single myocyte exposed to 0 to 10 μM CGS-21680 is given in FIG. 5. The agonists did not affect −dL/dt$_{max}$. The EC$_{50}$ of CGS-21680 was 6.10±2.0, 26.0±5.4, 48.2±6.7, 28.9±8.7 and 13.2±5.6 nM for LC, DS, TPS, TR and +dL/dt$_{max}$, respectively.

as indicated, every 10 min and the above contractile responses obtained. Asterisks denote a statistically significant difference from the appropriate zero CGS-21680 value.

Figure 6:
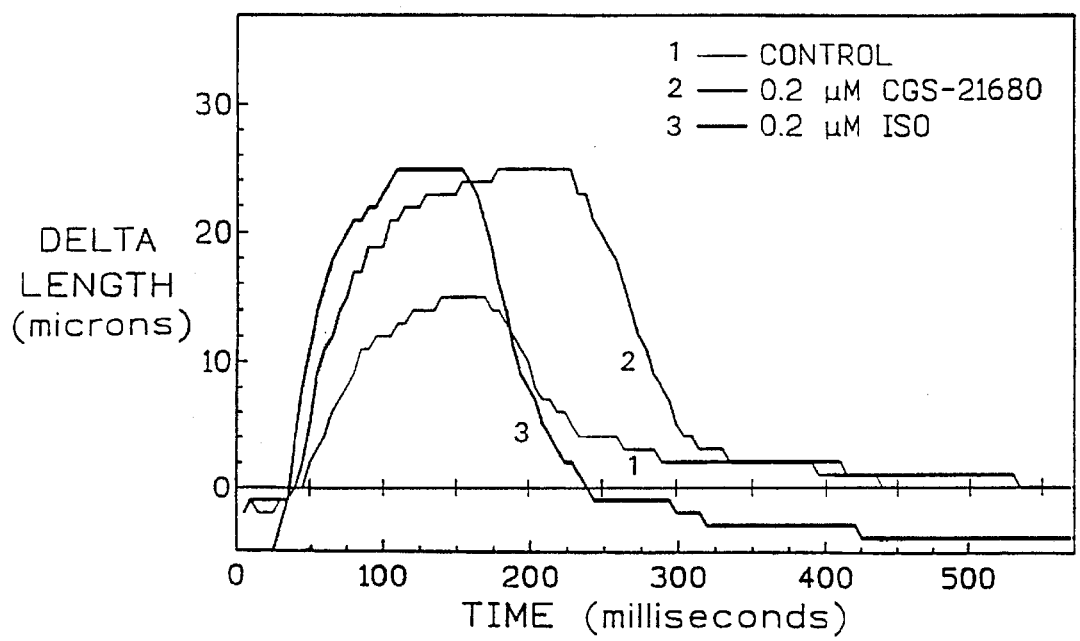
FIG. 6 is a graph comparing CGS-21680 and ISO elicited contractile responses in a rat ventricular myocyte. Traces are length changes associated with single contractile shortenings of a representative myocyte exposed to 0.2 μM CGS-21680 for 5 min., washed for 15 min in suffusion solution containing no CGS-21680 then exposed to 0.2 μM ISO for 3 min.

Both CGS-21680 and ISO increased the contractility of rat ventricular myocytes. This is illustrated in FIG. 6. The LC and +dL/dt$_{max}$ were increased by both agents (Tables 2 and 4). DS was increased with CGS-21680, but decreased with ISO. CGS-21680 increased TPS and TR, whereas ISO decreased these variables. CGS-21680 did not affect −dL/dt$_{max}$, but ISO increased this contractile variable.

Figure 7:
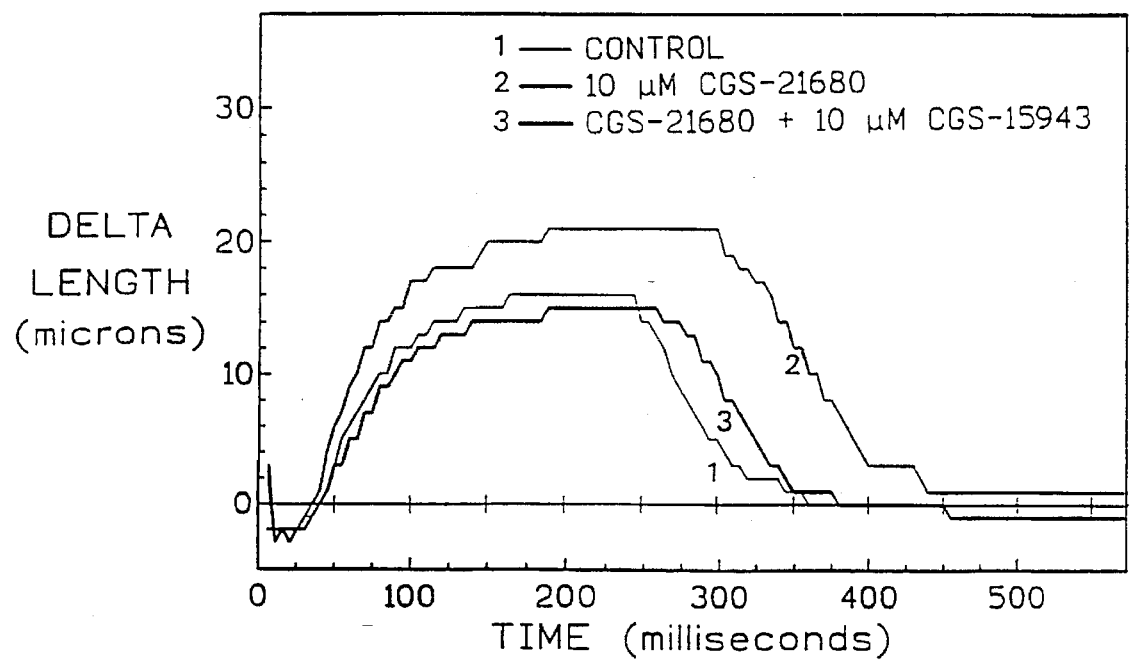
FIG. 7 is a graph illustrating the effect of CGS-21680 and 9-chloro-2-(2-furanyl)-5,6-dihydro-1,2,4-triazolo-(1,5-C)quinazolin-5-imine ("CGS-15943") on ventricular myocyte contraction. Traces are length changes associated with single contractile shortenings of a representative rat ventricular myocyte upon the sequential addition of 10 μM CGS-21680 and then 8–10 min later CGS-21680+10 μM CGS-15943.

Adenosine A$_2$ receptor antagonists inhibited the contractile responses elicited by CGS-21680 (Table 5). The adenosine A$_2$ receptor antagonist, CGS-15943 (10 μm) prevented the increase in myocyte contractility produced by the A$_2$ receptor agonist, CGS-21680 (10 μm). The inhibition by CGS-15943 of the CGS-21680 elicited increase in contractility for an individual myocyte is illustrated in FIG. 7. The A$_2$ receptor agonist, CGS-21680, at 1 μM in the presence of 0.2 μM DPCPX, caused no further increases in the contractility variables compared to 1 μM CGS-21680 administered in the absence of DPCPX (Tables 4 and 5). Moreover, the

TABLE 4

CONTRACTILE RESPONSES OF VENTRICULAR MYOCYTES TO CGS-21680

| CGS-21680 (M) | (N) | LC (μm) | DS (msec) | TPS (msec) | TR (msec) | +dL/dt$_{max}$ (μm/msec) | −dL/dt$_{max}$ (μm/msec) |
|---|---|---|---|---|---|---|---|
| 0 | 9 | 18 ± 1 | 326 ± 16 | 130 ± 4 | 297 ± 11 | 144 ± 12 | 124 ± 10 |
| 10$^{-8}$ | 8 | 22 ± 2 | 363 ± 15 | 144 ± 4* | 334 ± 10* | 162 ± 13 | 125 ± 11 |
| 10$^{-7}$ | 9 | 23 ± 2* | 431 ± 14* | 169 ± 3* | 361 ± 12* | 183 ± 14* | 126 ± 12 |
| 10$^{-6}$ | 9 | 24 ± 2* | 458 ± 12* | 183 ± 5* | 390 ± 13* | 188 ± 11* | 121 ± 15 |
| 10$^{-5}$ | 6 | 26 ± 3* | 460 ± 18* | 192 ± 4* | 397 ± 14* | 187 ± 13* | 127 ± 13 |
| 10$^{-4}$ | 6 | 22 ± 2 | 404 ± 17* | 156 ± 3* | 322 ± 12* | 158 ± 14 | 108 ± 16 |

Values are mean ± SE of the number of experiments indicated.

The data presented in Table 4 are from a cumulative dose-response experimental protocol. CGS-21680 was added to the suffusion solution at increasing concentrations, adenosine A$_2$ receptor antagonist, CSC, at 1 μM prevented the increase in the contractile variables elicited by 1 μM CGS-21680 in the presence of 0.2 μM DPCPX.

TABLE 5

ANTAGONISM OF CGS-21680-ELICITED VENTRICULAR MYOCYTE CONTRACTILE RESPONSES BY CGS-15943 AND CSC

| CONDITIONS | LC (μm) | DS (msec) | TPS (msec) | TR (msec) | +dL/dt$_{max}$ (μm/msec) | −dL/dt$_{max}$ (μm/msec) |
|---|---|---|---|---|---|---|
| CONTROL | 18 ± 1 | 330 ± 16 | 128 ± 4 | 290 ± 9 | 148 ± 12 | 118 ± 11 |
| 10$^{-5}$M CGS-21680 | 25 ± 2* | 486 ± 15* | 190 ± 4* | 392 ± 13* | 192 ± 11* | 122 ± 12 |

TABLE 5-continued

ANTAGONISM OF CGS-21680-ELICITED VENTRICULAR
MYOCYTE CONTRACTILE RESPONSES BY CGS-15943 AND CSC

| CONDITIONS | LC ($\mu$m) | DS (msec) | TPS (msec) | TR (msec) | $+dL/dt_{max}$ ($\mu$m/msec) | $-dL/dt_{max}$ ($\mu$m/msec) |
|---|---|---|---|---|---|---|
| $10^{-5}$M CGS-15943 | 18 ± 2 | 331 ± 15 | 122 ± 3 | 285 ± 10 | 146 ± 10 | 123 ± 11 |
| $10^{-5}$M CGS-21680 + $10^{-5}$M CGS-15943 | 19 ± 2† | 334 ± 14† | 129 ± 3† | 288 ± 12† | 149 ± 13† | 122 ± 10 |
| $10^{-6}$M CGS-21680 + $2 \times 10^{-7}$M DPCPX | 23 ± 1* | 456 ± 12* | 178 ± 5* | 361 ± 10* | 186 ± 10* | 120 ± 10 |
| $10^{-6}$M CSC + $2 \times 10^{-7}$M DPCPX | 18 ± 1 | 328 ± 13 | 126 ± 4 | 278 ± 11 | 135 ± 12 | 118 ± 9 |
| $10^{-6}$M CGS-21680 + $10^{-6}$M CSC + $2 \times 10^{-7}$M DPCPX | 17 ± 2† | 325 ± 14† | 123 ± 5† | 274 ± 13† | 132 ± 14† | 119 ± 10† |

Values are mean ± SE (N = 6).

CGS-21680, CGS-15943, DPCPX or CSC were added to the suffusion solution separately or in combination, as indicated, for 10 min. DPCPX at $2 \times 10^{-7}$M was present when CGS-21680 and CSC were used at $10^{-6}$M as indicated. Asterisks denote a statistically significant difference from the control value. Daggers denote a statistically significant difference from the appropriate CGS-21680 value in the absence of an adenosine $A_2$ receptor antagonist.

Two adenosine analogues, SHA-082 and NECA, as well as adenosine, increased contractility of ventricular myocytes. The responses were inhibited by an adenosine $A_2$ receptor antagonist. SHA-082 at 10 $\mu$M increased LC, DS, TPS, TR and $+dL/dt_{max}$ by 41, 64, 37, 40 and 30%, respectively (Table 6). NECA at the same concentration increased LC, DS, TPS and TR by 24, 21, 20 and 28%, respectively. The contractile responses elicited by NECA and SHA-082 were not observed in the presence of 10 $\mu$M CGS-15943. While 100 $\mu$M adenosine or 0.2 $\mu$M DPCPX were without effect when administered alone, the two agents when administered together caused 35, 20, 27, 37 and 29% increases in LC, DS, TPS, TR and $+dL/dt_{max}$, respectively. These adenosine induced increases were inhibited by 10 $\mu$M CGS-15943.

TABLE 6

CONTRACTILE RESPONSES OF RAT VENTRICULAR MYOCYTES
TO SHA-082, NECA AND ADENOSINE.

| CONDITIONS | LC ($\mu$m) | DS (msec) | TPS (msec) | TR (msec) | $+dL/dt_{max}$ ($\mu$m/msec) | $-dL/dt_{max}$ ($\mu$m/msec) |
|---|---|---|---|---|---|---|
| CONTROL | 17 ± 1 | 289 ± 15 | 117 ± 3 | 265 ± 10 | 181 ± 9 | 150 ± 10 |
| $10^{-5}$M SHA-082 | 24 ± 2* | 473 ± 17* | 160 ± 5* | 372 ± 13* | 236 ± 10* | 147 ± 9 |
| $10^{-5}$M SHA-082 + $10^{-5}$M CGS-15943 | 15 ± 1† | 322 ± 16† | 123 ± 4† | 263 ± 11† | 175 ± 11† | 153 ± 11 |
| $10^{-5}$M NECA | 21 ± 2* | 350 ± 15* | 140 ± 5* | 340 ± 12* | 203 ± 9 | 149 ± 12 |
| $10^{-5}$M NECA + $10^{-5}$M CGS-15943 | 16 ± 1† | 282 ± 14† | 115 ± 4† | 256 ± 14† | 191 ± 8 | 146 ± 10 |
| $2 \times 10^{-7}$M DPCPX | 17 ± 1 | 279 ± 15 | 116 ± 3 | 264 ± 11 | 179 ± 9 | 147 ± 11 |
| $10^{-4}$M ADENOSINE | 16 ± 1 | 293 ± 16 | 120 ± 4 | 281 ± 12 | 180 ± 10 | 151 ± 10 |
| $2 \times 10^{-7}$M DPCPX + $10^{-4}$M ADENOSINE | 23 ± 2* | 346 ± 13* | 149 ± 4* | 363 ± 10* | 234 ± 11* | 152 ± 12 |
| $2 \times 10^{-7}$M DPCPX + $10^{-4}$M ADENOSINE + $10^{-5}$M CGS-15943 | 15 ± 2† | 273 ± 14† | 115 ± 3† | 259 ± 13† | 185 ± 10† | 148 ± 10 |

Values are mean ± SE (N = 6).

In the experiment summarized in Table 6, each agent was added to the suffusion solution separately or in combination with CGS-15943 and/or DPCPX as indicated. Asterisks denote a statistically significant difference from the control value. Daggers denote a statistically significant difference from the corresponding value in the absence of CGS-15943.

Figure 8:
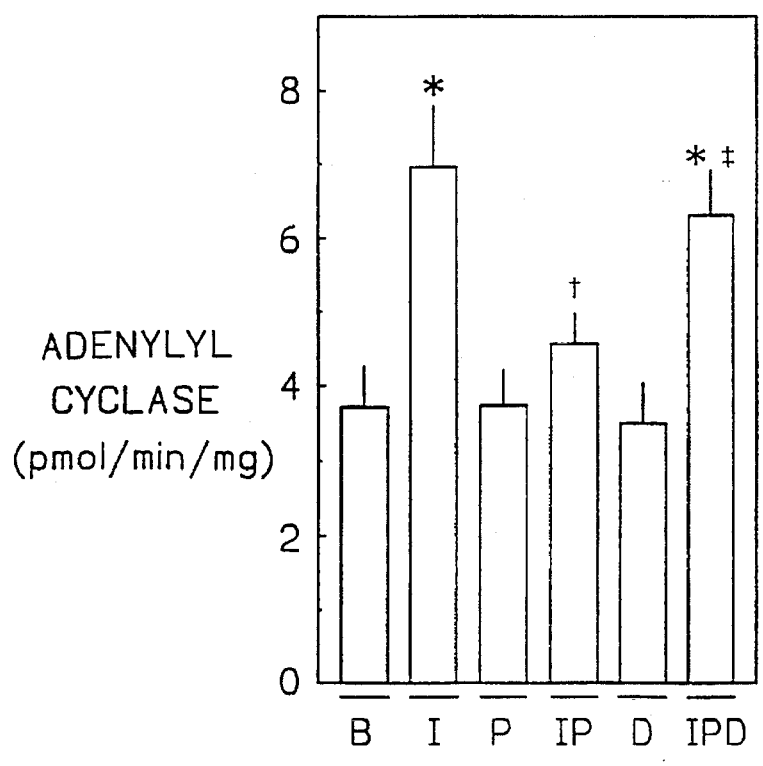
FIG. 8 is a graph illustrating the effect of PIA on ISO stimulated ventricular myocyte membrane adenylyl cyclase activity. Adenylyl cyclase activity was assessed in the absence (basal, B) or presence of 0.1 μM ISO (I), 0.1 μM PIA (P), 0.1 μM DPCPX (D) or a combination of these for 9 min as indicated. Each value represents the mean±SE of 13 different membrane preparations. Asterisks denote a statistically significant difference from the basal (B) value. The dagger denotes a statistically significant difference from the ISO (I) value. The double daggers denotes a statistically significant difference from the PIA+ISO (PI) value.

In membranes from the same ventricular myocyte preparations used for the above contractility studies, the PIA reduction of ISO stimulated adenylyl cyclase activity was prevented by DPCPX (FIG. 8). ISO at 0.1 µM caused increases in adenylyl cyclase activity of 88% in the absence and 23% in the presence of 1 µM PIA. DPCPX at 0.1 µM prevented the PIA inhibition thereby allowing a 70% ISO-induced increase in adenylyl cyclase activity.

Figure 9:
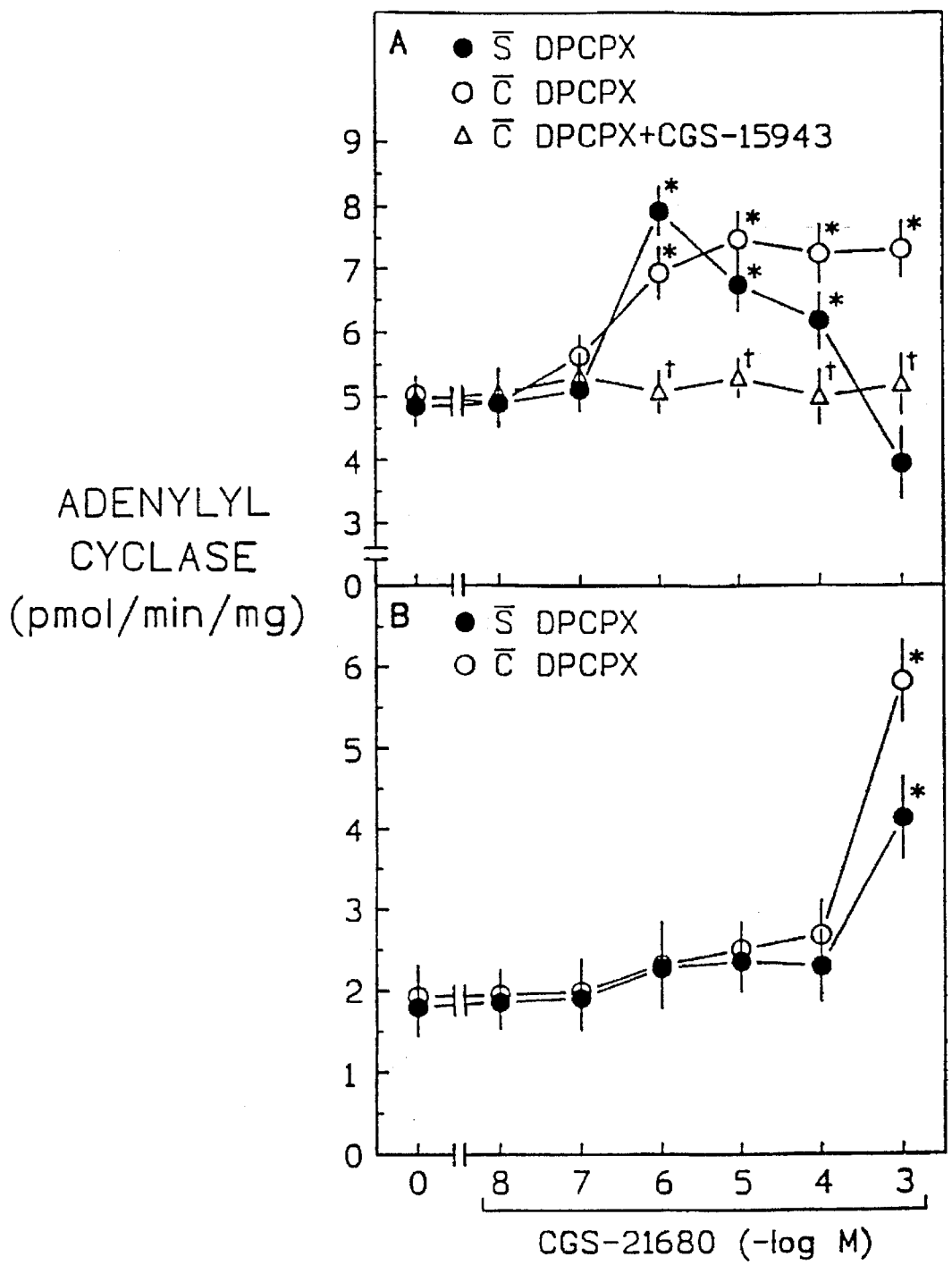
FIG. 9(A and B) are graphs illustrating the effect of CGS-21680 on ventricular myocyte (FIG. 9A) and myocardial (FIG. 9B) membrane adenylyl cyclase activities. Membrane adenylyl cyclase activity was assessed in the absence (●) or presence (○) of 0.1 μM DPCPX or DPCPX+10 μM CGS-15943 (Δ) at 0 to 1 mM CGS-21680, as indicated, for 9 min. Each value represents the mean±SE for 16 (FIG. 9A) and 14 (FIG. 9B) individual membrane preparations. Asterisks denote a statistically significant difference from the appropriate zero CGS-21680 value. Daggers denote a statistically significant difference from the corresponding value in the presence of DPCPX.

CGS-21680 increased adenylyl cyclase activity and the increase was prevented by CGS-15943. In a membrane preparation from ventricular myocytes CGS-26180 caused a biphasic response by activating adenylyl cyclase at low concentrations of 1–10 µM and reducing this activation at higher concentrations of 0.1–1 mM (FIG. 9A). However, in the presence of 0.1 µM DPCPX, CGS-21680 only increased adenylyl cyclase with an $EC_{50}$ of 0.26±0.08 µM. The latter increase in cyclase activity of 49% was prevented by 10 µM CGS-15943. When homogenate of the rat heart ventricular myocardium were used only 1 MM CGS-21680 increased asenylyl cyclase activity (FIG. 9B).

Figure 10:
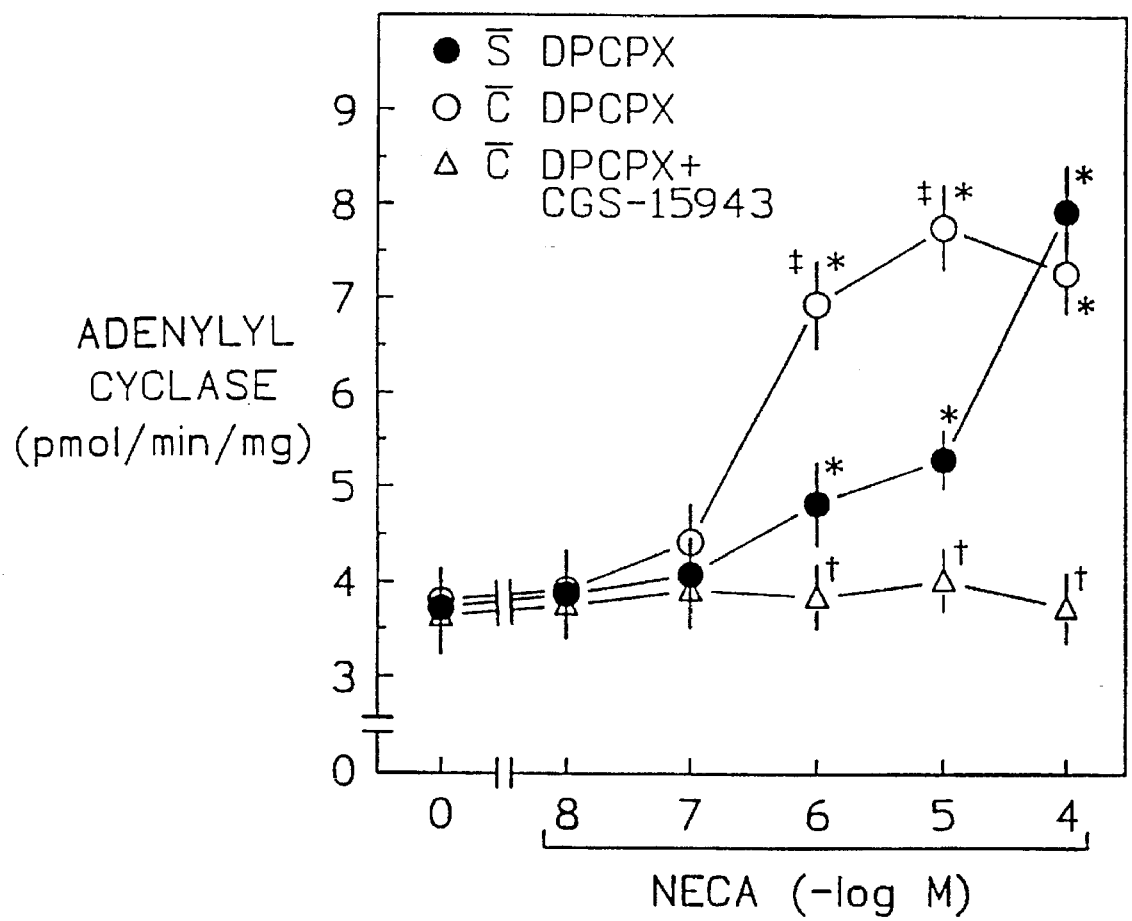
FIG. 10 is a graph illustrating the effect of N-ethylcarboxamidoadenosine ("NECA") on ventricular myocyte membrane adenylyl cyclase activity. Cyclase activity was assessed in the absence (●) or presence (○) of 0.1 μM DPCPX or DPCPX+10 μM CGS-15943 (Δ) at 0 to 1 mM NECA, as indicated, for 9 min. Each value represents the mean±SE for 11 individual membrane preparations. Asterisks denote a statistically significant difference from the appropriate zero NECA value. Daggers denote a statistically significant difference from the corresponding NECA values in the absence of CGS-15943. Double daggers denote a statistically significant difference from the corresponding NECA values in the absence of DPCPX.
Figure 11:
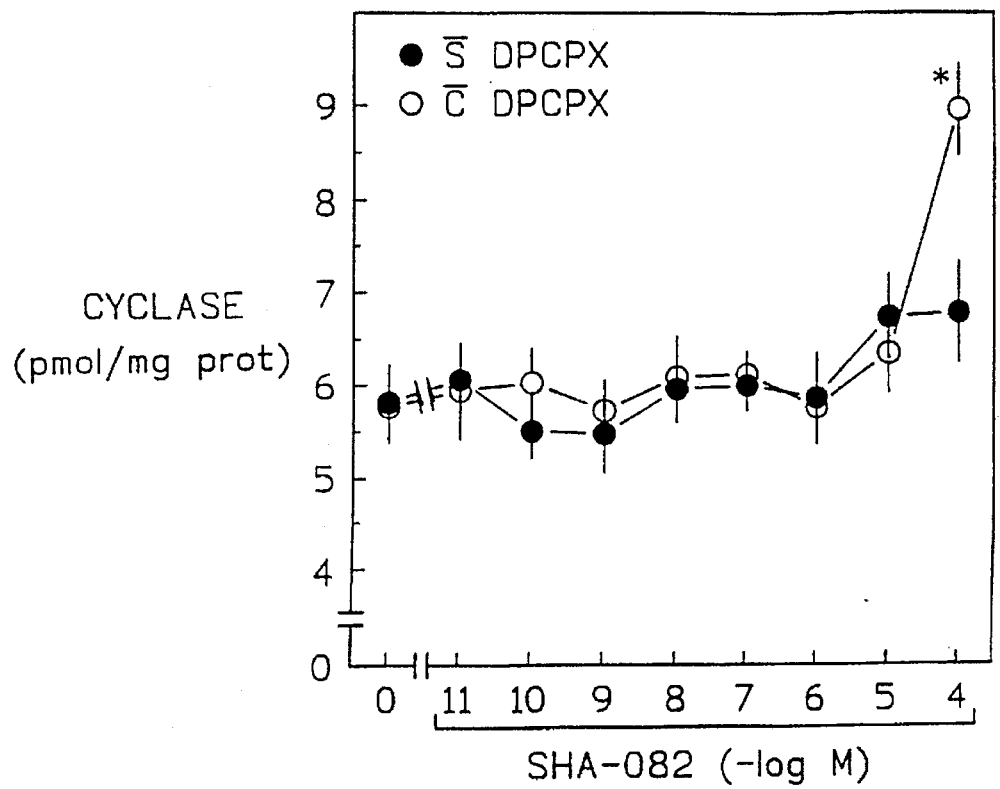
FIG. 11 is a graph illustrating the effect of naphthyl-substituted aralkoxyadenosine ("SHA-082") on ventricular myocyte membrane adenylyl cyclase activity. Cyclase activity was assessed in the absence (●) or presence (○) of 0.1 μM DPCPX at 0 to 0.1 mM SHA-082 for 9 min as indicated. Each value represents the mean±SE for 16 individual membrane preparations. The asterisk denotes a statistically significant difference from the appropriate zero SHA-082 value.
Figure 12:
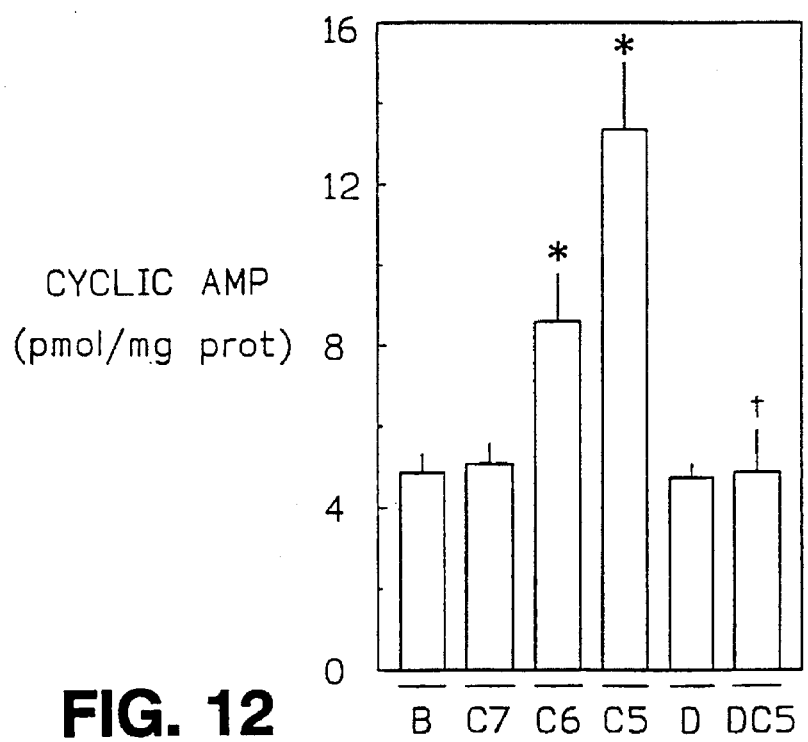
FIG. 12 is a graph illustrating the effect of CGS-21680 on cAMP content of cultured ventricular myocytes. Cultures were exposed for 10 min to 0 (B), 0.1 μM (C7), 1 μM (C6), or 10 μM (C5) CGS-21680, 1 μM 3,7-dimethyl-1-propargylxanthine ("DMPX") (D) or 1 μM DMPX plus 10 μM CGS-21680 (DC5). Myocyte cAMP levels were then determined as described in the Methods. Each value represents the mean±SE of 5 individual culture plates obtained from 16 separate preparations. Asterisks denote a statistically significant difference from basal (B). The dagger denotes a statistically significant difference from the corresponding C5 and C6 value.

NECA increased adenylyl cyclase activity by approximately two-fold (FIG. 10). The $EC_{50}$ value for activation of cyclase by NECA was 17.0±5.7 µM. However, in the presence of 0.1 µM DPCPX the $EC_{50}$ value for cyclase activation was 0.30±07 µM. CGS-15943 at 10 µM prevented the increase in membrane cyclase activity both in the absence and presence of the DPCPX. SHA-082 had minimal effect on adenylyl cyclase activity (FIG. 11). However, in the presence of 1 µM DPCPX SHA-082 increased adenylyl cyclase activity at a high concentration of 0.1 mM. In the presence of DPCPX the $EC_{50}$ for SHA-082 was approximately 15.5±0.5 µM. Adenosine at 0 to 1 mM in the absence or presence of 1 µM DPCPX did not increase adenylyl cyclase activity above basal levels is membranes obtained from ventricular myocytes or myocardium.

β-Adrenergic receptor stimulation with ISO at 0.1 and 1 µM for 1 minutes increased basal cultured ventricular myocyte cAMP (4.86 pmol/mg cell protein) by 90 and 138%, respectively. CGS-21680 at 1 and 10 µM for 10 minutes caused an increase in myocyte cAMP by 77 and 174%, respectively (FIG. 12). The $EC_{50}$ value for the $A_2$ agonist was 1.15±0.37 µM. The adenosine $A_2$ receptor antagonist, DMPX, prevented the increase in cAMP caused by 10 µM CGS-21680. SHA-082 at 0.1 to 10 µM had no effect on cAMP in cultured ventricular myocyte.

This study indicates the presence of both adenosine $A_1$ and $A_2$ receptors in the mammalian ventricular myocyte. In single isolated rat ventricular myocytes adenosine $A_1$ receptor stimulation was associated with the attenuation of β-adrenergic catecholamine induced contractile responses. Adenosine $A_2$ receptor stimulation alone was associated with positive inotropic responses in the myocytes.

The β-adrenergic catecholamine-elicited increases in myocyte length change (shortening), +dL/$dt_{max}$ and -dL/$dt_{max}$. Decreases in duration of shortening, time-to-peak shortening and time to 75% relaxation were attenuated by an adenosine $A_1$ receptor agonist, PIA. The attenuations caused by PIA were prevented by an adenosine $A_1$ receptor antagonist, DPCPX. Moreover, the results indicate that the antiadrenergic action of adenosine can be observed in a single contracting ventricular myocyte and does not require the presence of other myocardial cell types for its action. PIA alone did not affect myocyte contractility. This indicates that the adenosine $A_1$ receptor mediated attenuation of ventricular myocyte contractility is only observed in the presence of β-adrenergic catecholamine stimulation.

Adenosine $A_2$ receptor agonists produced positive inotropic responses in contracting ventricular myocytes. CGS-21680 caused a concentration-dependent increase in ventricular myocyte contractility. The agonist increased the length change, duration of shortening, time to peak shortening, time to 75% relaxation and +dL/$dt_{max}$ with values for $EC_{50}$ ranging from 6–48 nM for these contractile variables. NECA, SHA-082 and adenosine also increased myocyte contractility. However, adenosine required the presence of DPCPX to enhance myocyte contractility. The adenosine $A_2$ receptor antagonist CGS-15943 prevented the contractile responses elicited by the $A_2$ receptor agonists. It is particularly interesting that $A_2$-adenosinergic agonists increased +dL/$dt_{max}$ without affecting -dL/$dt_{max}$.

The above results indicate that adenosine $A_2$ receptor stimulation increases contractility in mammalian ventricular myocytes. Further evidence supporting adenosine $A_2$ receptor involvement is that $A_2$ receptor involvement is that $A_1$ receptor antagonist administration did not alter the contractile responses caused by $A_2$ receptor agonists. Moreover, the increase in contractility caused by low concentrations (~1 µM) of CGS-21680 were antagonized by low concentrations of a selective adenosine $A_{2a}$ receptor antagonist, CSC. This suggests that the $A_2$-adenosinergic-elicited positive inotropic responses observed were primarily mediated by adenosine $A_{2a}$ receptor stimulation.

There are several differences between the positive inotropic responses caused by β-adrenergic and $A_2$-adenosinergic stimulation of ventricular myocytes. While β and $A_2$ receptor stimulation each increased the length change and +dL/$dt_{max}$, the duration of shortening and time to 75% relaxation were decreased by β-adrenergic stimulation, but increased by $A_2$-adenosinergic stimulation. β-Adrenergic stimulation increased the maximum rate of relaxation—dL/$dt_{max}$ whereas $A_2$-adenosinergic stimulation did not affect this contractile variable. The differences between adrenergic and adenosinergic-induced contractile responses suggest the inotropic responses are mediated by different mechanisms. The $A_2$-adenosinergic induced inotropic response was not an abbreviated contraction as is observed with β-adrenergic stimulation. Thus, the positive inotropic response by $A_2$-adenosinergic stimulation is reminiscent of the inotropic response observed with an increase in extracellular $Ca^{2+}$ concentration.

Studies on Isolated Mammalian Hearts

Male Sprague-Dawley rats (500–550 g) were anesthetized with pentobarbital (40 mg/kg, i.p.) and treated with heparin (500 units, i.p.) for 15 minutes. Hearts were excised, rinsed in iced physiological saline ("PS") and perfused with PS (37° C.) via an aortic cannula at a constant rate of 18–20 ml/min. Perfusion pressure ranged from 50 to 60 mm Hg. The PS contained: NaCl, 118 mM; KCl, 4.7 mM; $CaCl_2$, 2.5 mM; $NaHCO_3$, 25 mM; $KH_2PO_4$, 1.2 mM; $MgSO_4$ 1.2 mM; glucose 10 mM; and pyruvate 1.8 mM. The pH was maintained at 7.4 by gassing the PS with a 95% $O_2$/5% $CO_2$ gas mixture. Platinum wire electrodes were inserted into the right atrium to allow pacing of the heart (300 contractions per minute) throughout the perfusion period. Developed left ventricular pressure (LVP) was measured with a saline-filled balloon inserted into the lumen of the left ventricle via the left atrium and attached by a polyethylene cannula to a pressure transducer. The pressure signal was electronically differentiated to obtain the maximum rates of left ventricular pressure development (+dP/dt$_{max}$) and relaxation (–dP/dt$_{max}$). Balloon volume was varied until the maximal obtainable dP/dt was attained. This optimal preload, ranging from 5 to 10 mm Hg, was maintained constant, permitting isovolumic contraction of the heart. Aortic perfusion pressure was monitored with another pressure transducer. All the LVP, +dP/dt$_{max}$, –dP/dt$_{max}$ and aortic perfusion data were continually recorded on a multichannel polygraph. At the end of the experiment, the wet heart weights were determined; they ranged from 1.4 to 1.8 g.

After instrumentation, the hearts were normoperfused at 18–20 ml/min for 20 minutes, resulting in an aortic perfusion pressure of 50–60 mm Hg. Isoproterenol, adenosine, CGS-21680, DPCPX, atenolol, or a combination of these agents was administered for 1 to 2 minutes, via the aortic perfusion cannula, at 1/100th the perfusion flow rate, to achieve the stated PS concentrations. Isoproterenol was administered for only 5 seconds. To cause mechanical depression of the perfused hearts, the perfusion flow was lowered 5–6 ml/min. The resulting aortic perfusion pressure decreased to 20–30 mm Hg. The various agents either alone or in combination were administered via the PS to the hypoperfused hearts at 1/100th the perfusion flow rate, at the concentrations indicated.

Figure 13:
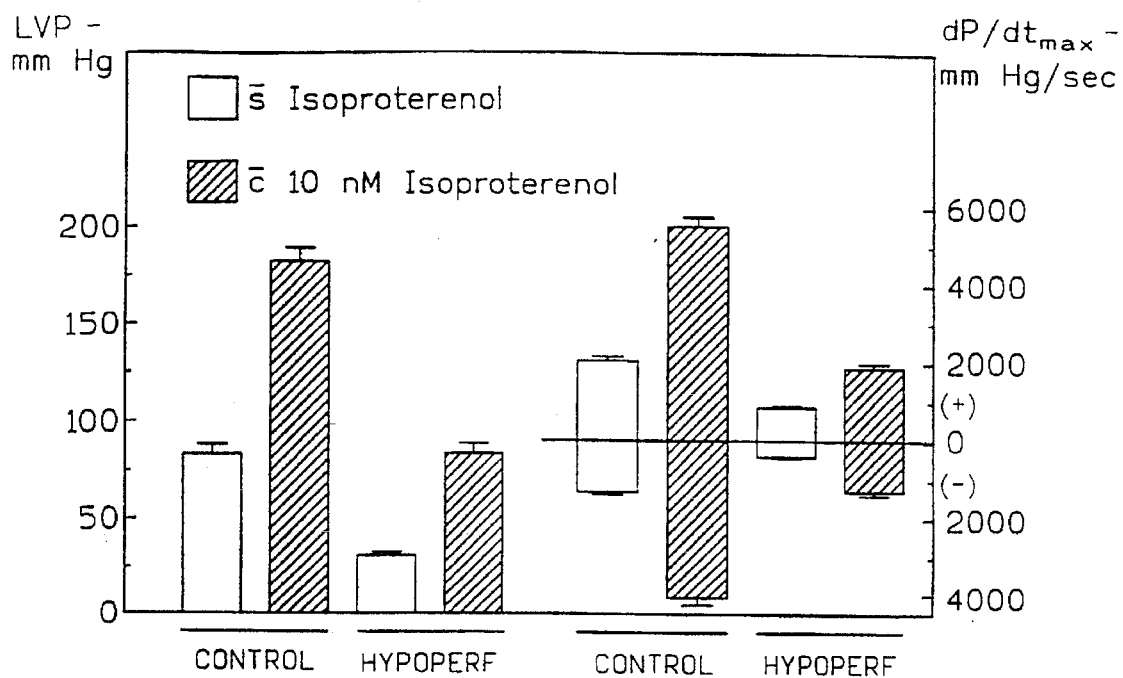
FIG. 13 is a graph illustrating the effect of $10^{-8}$M isoproterenol (5 sec.) on LVP, +dP/dt$_{max}$ and −dP/dt$_{max}$ in the normoperfused (control) and hypoperfused (hypoperf) mechanically depressed rat heart. The values are the mean±SE of six administrations performed in four hearts. The hypoperfused values are statistically different from the corresponding normoperfused values.

During normoperfusion, isoproterenol ($10^{-8}$M), a β-adrenergic catecholamine agonist, increased LVP, +dP/dt$_{max}$ and –dP/dt$_{max}$ by 119, 167 and 216%, respectively (FIG. 13). Adenosine ($2\times10^{-5}$M), adenosine+DPCPX ($2\times10^{-7}$M), an adenosine A$_1$ receptor antagonist did not affect the contractile variables. CGS-21680 ($2\times10^{-6}$M), an adenosine A$_2$ receptor agonist, also was without affect on the contractile variables.

Figure 14:
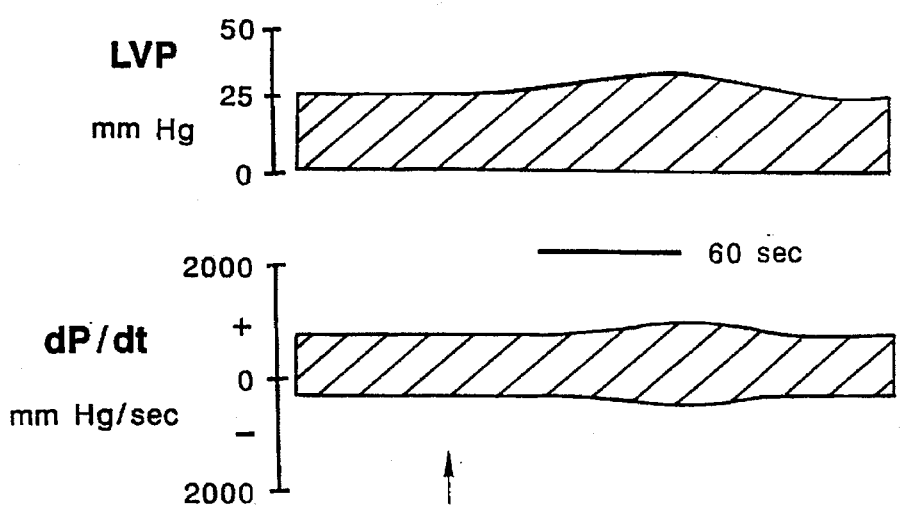
FIG. 14 is a depiction of a typical pressure recording illustrating the effect of $2\times10^{-5}$M adenosine plus $2\times10^{-7}$M DPCPX on LVP, +dP/dt$_{max}$ and −dP/dt$_{max}$ of the mechanically depressed (by hypoperfusion) rat heart. The adenosine and DPCPX were administered for 1.5 minutes from the time indicated by the arrow.
Figure 15:
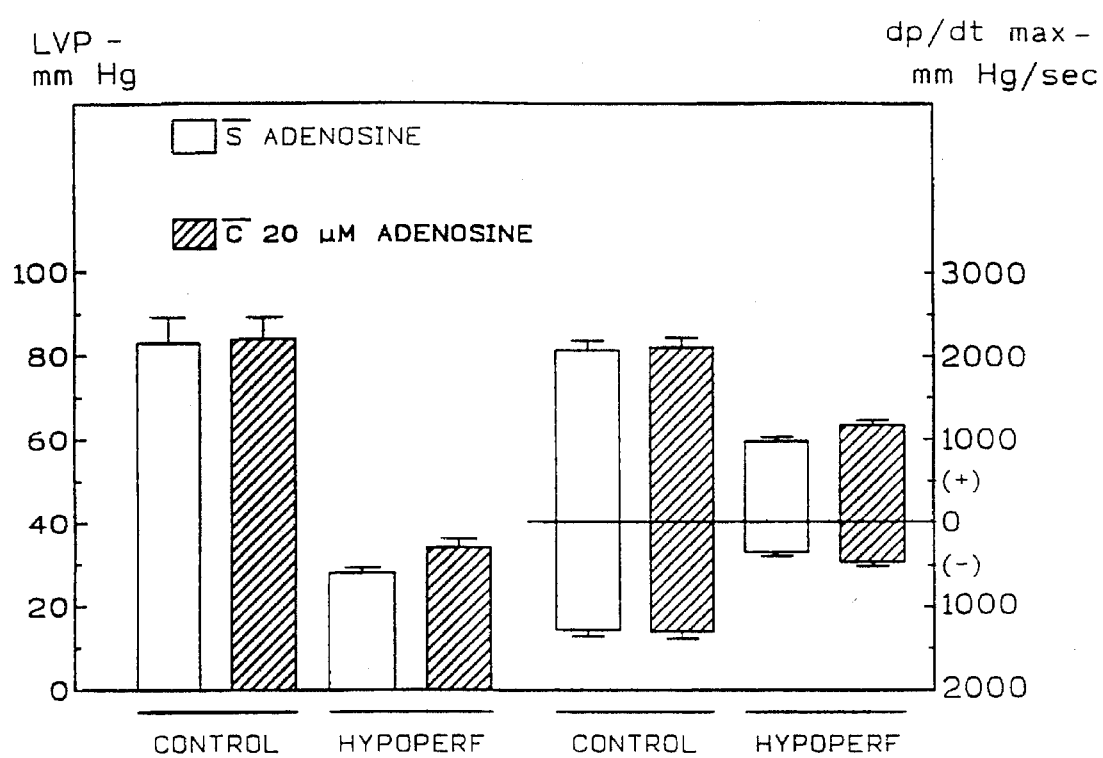
FIG. 15 is a graph illustrating the effect of $2\times10^{-5}$M adenosine plus $2\times10^{-7}$M DPCPX (1–2 min.) on LVP, dP/dt$_{max}$ and −dP/dt$_{max}$ in the normoperfused (control) and hypoperfused (hypoperf) mechanically depressed rat heart. The values are the mean±SE of six administrations performed in four hearts. The adenosine treatment values in the hypoperfused hearts are statistically different from the corresponding control values with adenosine.

With hypoperfusion, the contractile variables decreased, indicating myocardial depression, as reflected by a 63, 57 and 70% decrease in LVP, +dP/dt$_{max}$ and –dP/dt$_{max}$, respectively (FIG. 13). During hypoperfusion, adenosine plus DPCPX increased LVP, +dP/dt$_{max}$ and –dP/dt$_{max}$ by 21, 20 and 31%, respectively (FIGS. 14 and 15). FIG. 14 illustrates the typical positive inotropic responses elicited by adenosine plus DPCPX. Adenosine administration alone increased the contractile variables by 26, 25 and 33%. During the hypoperfusion period isoproterenol increased the three contractile variables by 171, 114 and 225% (FIG. 13). Administration of atenolol, a β-adrenergic antagonist, completely prevented the isoproterenol elicited contractile responses, but did not affect the inotropic responses induced by adenosine or adenosine plus DPCPX. This suggests that the positive inotropic action of adenosine was not due to the release of myocardial catecholamines.

These results indicate that adenosine, acting via an adenosine A$_2$ receptor, is capable of serving as a positive inotrop in a compromised mammalian myocardium. When the adenosine A$_1$ receptors were blocked, the inotropic effects of adenosine were maximal.

Reducing aortic perfusion flow from 18–20 ml/min to 5–6 ml/min caused a 57–63% reduction of the three contractile variables. This is a form of mechanical depression of the heart, presumably due to the insufficient delivery of O$_2$ and glucose/pyruvate to the myocardium. This model of heart failure could be equated to ischemia induced failure where blood supply to the myocardium is limited or myocardial hypertrophy.

Mammalian Heart Models

The rodent heart is a well-recognized model for investigating human cardiovascular physiology. In particular, the rodent heart and the human heart have been shown to respond similarly to adenosine, with respect to various parameters. For example, similar coronary vasodilation in response to adenosine has been observed in the human heart and the rat heart (Berne, Circ. Res. 47:807 (1980)). Also, adenosine bound to A$_1$ receptors has been shown to be antiarrthymogenic in both human and rat hearts (Belardinelli et al., Circ. Res. 51:569 (1982)). In addition, adenosine has an antiadrenergic action in both the human and the guinea pig myocardium (Bohm et al., Eur. J. Pharmacol. 116:323 (1985)).

Experimental Materials

ISO was purchased from Sigma Chemical Co. (St. Louis, Mo.). PIA, NECA, DPCPX, CSC, CGS-21680, CGS-15943, and DMPX were purchased from Research Biochemicals (Natick, Mass.). CGS-15943 was initially obtained from Dr. R. A. Lovell of Ciba-Geigy (Summit, N.J.). SHA-082 was synthesized by Dr. R. A. Olsson of the Univ of South Florida (Tampa, Fla.). [α-$^{32}$P]dATP (800 Ci/mmol) was purchased from Amersham (Arlington Heights, Ill.) and [$^3$H]dcAMP (5.2 Ci/mmol) was purchased from ICN Pharmaceuticals (Irving, Calif.).

Stock solutions of PIA, CSC, DPCPX, CGS-21680, CGS-15943, and SHA-082 (10 mM) were prepared in DMSO. ISO (10 mM) was prepared in the appropriate buffer containing 1 mM ascorbic acid. NECA (1 mM), DMPX (1 mM) and adenosine (10 mM) were prepared in distilled/deionized water. Stock solutions were serially diluted with the appropriate buffers to the desired concentrations.

Other embodiments of the invention are within the following claims.

We claim:

1. A method for increasing the contractile performance of a compromised myocardium in a mammal, comprising administering a therapeutically effective amount of an adenosine A$_2$ receptor agonist other than adenosine to said mammal.

2. The method of claim 1, wherein said mammal is a human.

3. The method of claim 1, wherein said compromised myocardium is ischemic.

4. The method of claim 1, wherein said compromised myocardium is hypoxic.

5. The method of claim 1, wherein said compromised myocardium is hypertrophied.

6. The method of claim 1, wherein said compromised myocardium is compromised as a result of unknown causes.

7. The method of claim 1, wherein said adenosine A$_2$ receptor agonist is selected from the group consisting of CGS-21680, NECA, SRA-082, 5'-(N-cyclopropyl)-carboxamido-adenosine and DPMA (PD-125944).

8. The method of claim 1, wherein said adenosine A$_2$ receptor agonist is administered intravenously.

9. The method of claim 1, further comprising administering to said mammal, in conjunction with an adenosine A$_2$ receptor agonist, a therapeutically effective amount of a second compound which potentiates the therapeutic effect of the adenosine A$_2$ receptor agonist.

10. The method of claim 9, wherein said second compound enhances the myocardial concentration of adenosine.

11. The method of claim 10, wherein said myocardial concentration of adenosine is enhanced by inhibiting clearance of interstial adenosine in the myocardium.

12. The method of claim 11, wherein said clearance of interstitial adenosine is inhibited by an adenosine transport inhibitor.

13. The method of claim 12, wherein said adenosine transport inhibitor is selected from the group consisting of dipyridamole, nitrobenzylthioinosine, nitrobenzylthioguanosine and Draflazine.

14. The method of claim 10, wherein said second compound is an adenosine deaminase inhibitor.

15. The method of claim 14, wherein said adenosine deaminase inhibitor is EHNA.

16. The method of claim 10, wherein said second compound is an adenosine kinase inhibitor.

17. The method of claim 16, wherein said adenosine kinase inhibitor is iodotubercidin.

18. The method of claim 9, wherein said second compound is an adenosine $A_1$ receptor antagonist.

19. The method of claim 18, wherein said adenosine $A_1$ receptor antagonist is selected from the group consisting of 1-allyl-3,7-dimethyl-8-phenyl-xanthine, 8-cyclopentyl-1,3-dimethylxanthine, 8-cyclopentyl-1,3-dipropylxanthine ("DPCPX"), 1,3-diethyl-8-phenylxanthine, 8-phenyltheophylline and xanthine amine congener ("XAC").

20. The method of claim 1, wherein said administering is continuous, for an indefinite period.

21. The method of claim 9, wherein said administering is continuous, for an indefinite period.

* * * * *